US007078507B2

(12) United States Patent
Narum et al.

(10) Patent No.: US 7,078,507 B2
(45) Date of Patent: Jul. 18, 2006

(54) SYNTHETIC GENES FOR MALARIAL PROTEINS AND METHODS OF USE

(75) Inventors: David Narum, Gaithersburg, MD (US); Hong Liang, Gaithersburg, MD (US); Steve Fuhrmann, Germantown, MD (US); B. Kim Lee Sim, Gaithersburg, MD (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 10/293,913

(22) Filed: Nov. 12, 2002

(65) Prior Publication Data
US 2004/0022805 A1      Feb. 5, 2004

Related U.S. Application Data

(60) Provisional application No. 60/345,051, filed on Nov. 9, 2001.

(51) Int. Cl.
  *C12N 15/30* (2006.01)
  *C12N 15/09* (2006.01)
  *C07H 21/04* (2006.01)
  *A61K 39/015* (2006.01)
  *C07K 14/445* (2006.01)

(52) U.S. Cl. .................. 536/23.1; 435/69.3; 435/69.7; 536/23.5; 536/23.7; 424/268.1; 424/272.1; 530/350

(58) Field of Classification Search ............... 536/23.5, 536/23.1, 23.7; 424/268.1, 272.1; 530/350; 435/69.3, 69.7; 514/44
See application file for complete search history.

(56) References Cited

U.S. PATENT DOCUMENTS 5,849,306 A * 12/1998 Sim et al. ................ 424/268.1
6,392,026 B1 * 5/2002 Sim et al. .................. 536/23.5

OTHER PUBLICATIONS

Rudinger et al, in "Peptide Hormones", edited by Parsons, J.A., University Park Press, Jun. 1976.*
Biochemical and Biophysical Research Communications 1999, 261; 445-451.*
GeneEmbl, Accession No. PFU27384 or PFU 78724.*
Kim et al 1997, Molecular and Biochemical Parasitology 1997, 84: 241-24.*
Narum et al., "Codon Optimization of Gene Fragments Encoding *Plasmodium falciparum* Merzoite Proteins Enhances DNA VAccine Protein Expression and Immunogenicity in Mice," *Infection and Immunity* (2001), vol. 69, No. 12, pp. 7250-7253.
Liang and Sim, 1997, "Conservation of structure and function of the erythrocyte-binding domain of *Plasmodium falciparum* EBA-175," *Mol Biochem Parasitol* 84: 241.

* cited by examiner

*Primary Examiner*—Lynette R. F. Smith
*Assistant Examiner*—Padma Baskar
(74) *Attorney, Agent, or Firm*—Knobbe, Martens, Olson & Bear, LLP

(57) ABSTRACT

Synthetic gene sequences encoding erythrocyte binding protein of a malaria pathogen for the expression of the erythrocyte binding protein. The codon composition of the synthetic gene sequences approximates the mammalian codon composition. The synthetic gene sequences are useful for incorporation into the DNA vaccine vectors, for the incorporation into various expression vectors for production of malaria proteins, or both. The synthetic genes may be modified to avoid post-translational modification of the encoded protein in hosts. Administration of the synthetic gene sequences, or the encoded protein, as an immunization agent is useful for induction of immunity against malaria, treatment of malaria, or both.

3 Claims, 15 Drawing Sheets

A

Region I        II         III, IV, V      VI  VII signal   F1        F2                    3 'Cys    *P. falciparum*
                                                   EBA-175

A
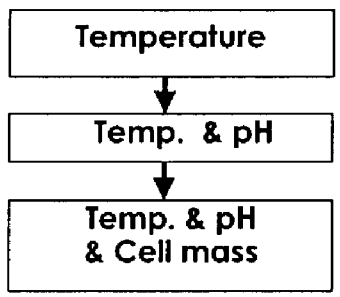
B
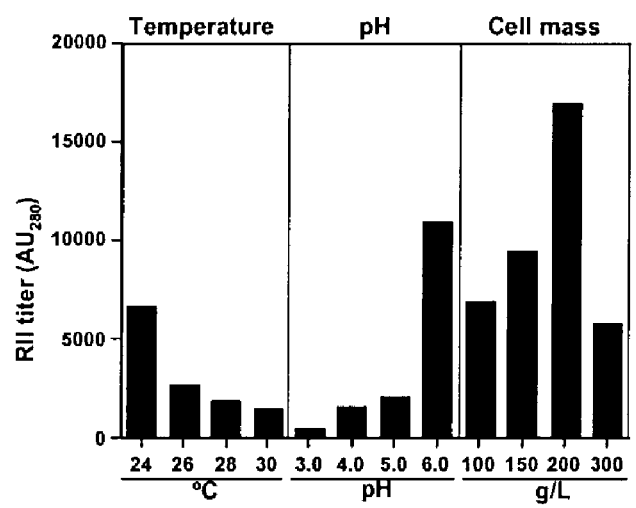
Figure 3

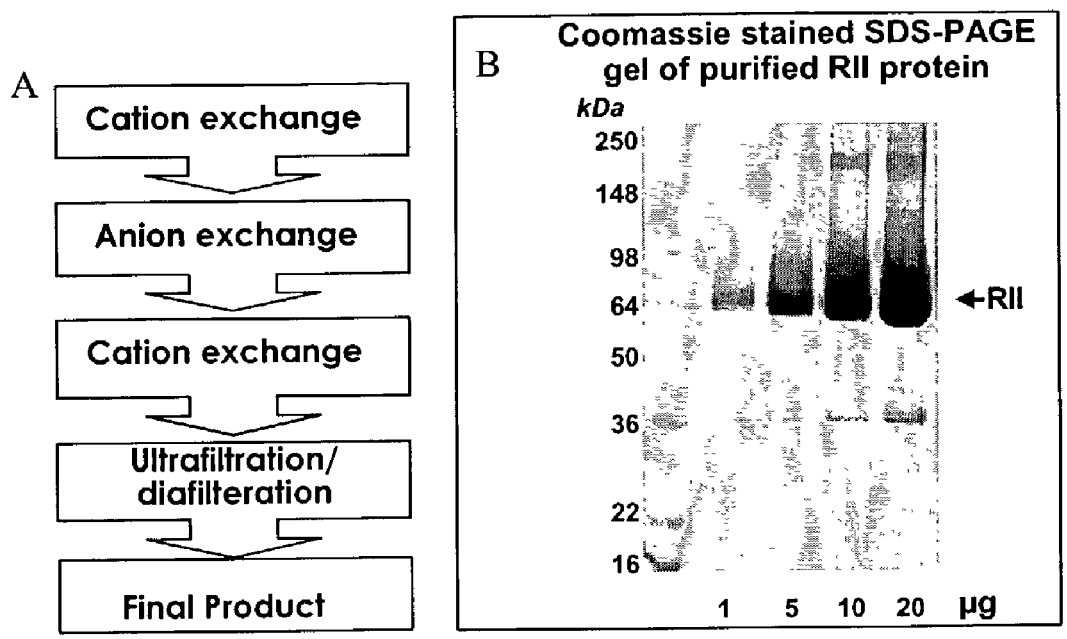
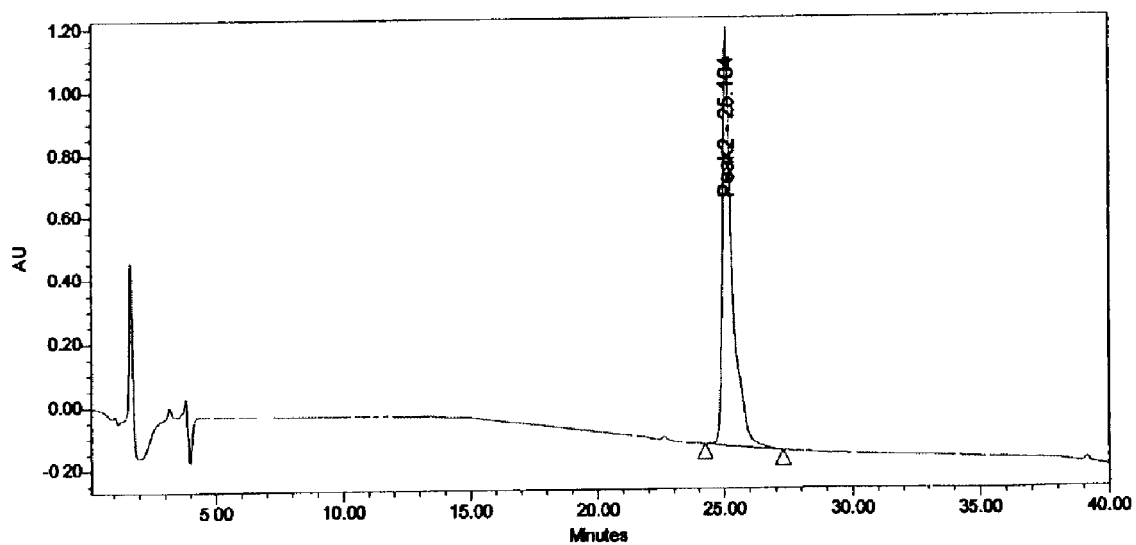
Figure 4

Region  I        II              III, IV, V        VI    VII

F1          F2                                      EBA-175 signal

|  | AMINO ACID | | | |
|---|---|---|---|---|
|  | 1<br>4<br>7 | 1<br>9<br>4 | 3<br>3<br>9 | 3<br>5<br>0 | 5<br>4<br>4 |

NATIVE:
PfEBA-175 RII           NTS NLS NRS NNT NKT

MUTATED:
PfEBA-175 RII-N-gly     QTS NLA NRA NNA QKT

Figure 5

```
GGCCGCAACACCTCCTCCAACAACGAGGTGCTGTCCAACTGCCGCGAGAAGCGCAAGGGCATGAAGTGGGA
CTGCAAGAAGAAGAACGACCGCTCCAACTACGTGTGCATCCCCGACCGCCGCATCCAGCTGTGCATCGTGA
ACCTGTCCATCATCAAGACCTACACCAAGGAGACCATGAAGGACCACTTCATCGAGGCCTCCAAGAAGGAG
TCCCAGCTGCTGCTGAAGAAGAACGACAACAAGTACAACTCCAAGTTCTGCAACGACCTGAAGAACTCCTT
CCTGGACTACGGCCACCTGGCCATGGGCAACGACATGGACTTCGGCGGCTACTCCACCAAGGCCGAGAACA
AGATCCAGGAGGTGTTCAAGGGCGCCCACGGCGAGATCTCCGAGCACAAGATCAAGAACTTCCGCAAGAAG
TGGTGGAACGAGTTCCGCGAGAAGCTGTGGGAGGCCATGCTGTCCGAGCACAAGAACAACATCAACAACTG
CAAGAACATCCCCCAGGAGGAGCTGCAGATCACCCAGTGGATCAAGGAGTGGCACGGCGAGTTCCTGCTGG
AGCGCGACAACCGCTCCAAGCTGCCCAAGTCCAAGTGCAAGAACAACACCCTGTACGAGGCCTGCGAGAAG
GAGTGCATCGACCCCTGCATGAAGTACCGCGACTGGATCATCCGCTCCAAGTTCGAGTGGCACACCCTGTC
CAAGGAGTACGAGACCCAGAAGGTGCCCAAGGAGAACGCCGAGAACTACCTGATCAAGATCTCCGAGAACA
AGAACGACGCCAAGGTGTCCCTGCTGCTGAACAACTGCGACGCCGAGTACTCCAAGTACTGCGACTGCAAG
CACACCACCACCCTGGTGAAGTCCGTGCTGAACGGCAACGACAACACCATCAAGGAGAAGCGCGAGCACAT
CGACCTGGACGACTTCTCCAAGTTCGGCTGCGACAAGAACTCCGTGGACACCAACACCAAGGTGTGGGAGT
GCAAGAAGCCCTACAAGCTGTCCACCAAGGACGTGTGCGTGCCCCCCGCCGCCAGGAGCTGTGCCTGGGC
AACATCGACCGCATCTACGACAAGAACCTGCTGATGATCAAGGAGCACATCCTGGCCATCGCCATCTACGA
GTCCCGCATCCTGAAGCGCAAGTACAAGAACAAGGACGACAAGGAGGTGTGCAAGATCATCAACAAGACCT
TCGCCGACATCCGCGACATCATCGGCGGCACCGACTACTGGAACGACCTGTCCAACCGCAAGCTGGTGGGC
AAGATCAACACCAACTCCAACTACGTGCACCGCAACAAGCAGAACGACAAGCTGTTCCGCGACGAGTGGTG
GAAGGTGATCAAGAAGGACGTGTGGAACGTGATCTCCTGGGTGTTCAAGGACAAGACCGTGTGCAAGGAGG
ACGACATCGAGAACATCCCCCAGTTCTTCCGCTGGTTCTCCGAGTGGGGCGACGACTACTGCCAGGACAAG
ACCAAGATGATCGAGACCCTGAAGGTGGAGTGCAAGGAGAAGCCCTGCGAGGACGACAACTGCAAGCGCAA
GTGCAACTCCTACAAGGAGTGGATCTCCAAGAAGAAGGAGGAGTACAACAAGCAGGCCAAGCAGTACCAGG
AGTACCAGAAGGGCAACAACTACAAGATGTACTCCGAGTTCAAGTCCATCAAGCCCGAGGTGTACCTGAAG
AAGTACTCCGAGAAGTGCTCCAACCTGAACTTCGAGGACGAGTTCAAGGAGGAGCTGCACTCCGACTACAA
GAACAAGTGCACCATGTGCCCCGAGGTGAAGGACGTGCCCATCTCCATCATCCGCAACAACGAGCAGACCT
CC
```

Figure 6

```
GRNTSSNNEVLSNCREKRKGMKWDCKKKNDRSNYVCIPDRRIQLCIVNLSIIKTYTKETMKDHFIEASKKE
SQLLLKKNDNKYNSKFCNDLKNSFLDYGHLAMGNDMDFGGYSTKAENKIQEVFKGAHGEISEHKIKNFRKK
WWNEFREKLWEAMLSEHKNNINNCKNIPQEELQITQWIKEWHGEFLLERDNRSKLPKSKCKNNTLYEACEK
ECIDPCMKYRDWIIRSKFEWHTLSKEYETQKVPKENAENYLIKISENKNDAKVSLLLNNCDAEYSKYCDCK
HTTTLVKSVLNGNDNTIKEKREHIDLDDFSKFGCDKNSVDTNTKVWECKKPYKLSTKDVCVPPRRQELCLG
NIDRIYDKNLLMIKEHILAIAIYESRILKRKYKNKDDKEVCKIINKTFADIRDIIGGTDYWNDLSNRKLVG
KINTNSNYVHRNKQNDKLFRDEWWKVIKKDVWNVISWVFKDKTVCKEDDIENIPQFFRWFSEWGDDYCQDK
TKMIETLKVECKEKPCEDDNCKRKCNSYKEWISKKKEEYNKQAKQYQEYQKGNNYKMYSEFKSIKPEVYLK
KYSEKCSNLNFEDEFKEELHSDYKNKCTMCPEVKDVPISIIRNNEQTS
```

Figure 7

```
GGCCGCcagACCTCCTCCAACAACGAGGTGCTGTCCAACTGCCGCGAGAAGCGCAAGGGCATGAAGTGGGACTGCAAGA
AGAAGAACGACCGCTCCAACTACGTGTGCATCCCCGACCGCCGCATCCAGCTGTGCATCGTGAACCTGgCCATCATCAA
GACCTACACCAAGGAGACCATGAAGGACCACTTCATCGAGGCCTCCAAGAAGGAGTCCCAGCTGCTGCTGAAGAAGAAC
GACAACAAGTACAACTCCAAGTTCTGCAACGACCTGAAGAACTCCTTCCTGGACTACGGCCACCTGGCCATGGGCAACG
ACATGGACTTCGGCGGCTACTCCACCAAGGCCGAGAACAAGATCCAGGAGGTGTTCAAGGGCGCCCACGGCGAGATCTC
CGAGCACAAGATCAAGAACTTCCGCAAGAAGTGGTGGAACGAGTTCCGCGAGAAGCTGTGGGAGGCCATGCTGTCCGAG
CACAAGAACAACATCAACAACTGCAAGAACATCCCCCAGGAGGAGCTGCAGATCACCCAGTGGATCAAGGAGTGGCACG
GCGAGTTCCTGCTGGAGCGCGACAACCGCgCCAAGCTGCCCAAGTCCAAGTGCAAGAACAACgCCCTGTACGAGGCCTG
CGAGAAGGAGTGCATCGACCCCTGCATGAAGTACCGCGACTGGATCATCCGCTCCAAGTTCGAGTGGCACACCCTGTCC
AAGGAGTACGAGACCCAGAAGGTGCCCAAGGAGAACGCCGAGAACTACCTGATCAAGATCTCCGAGAACAAGAACGACG
CCAAGGTGTCCCTGCTGCTGAACAACTGCGACGCCGAGTACTCCAAGTACTGCGACTGCAAGCACACCACCACCCTGGT
GAAGTCCGTGCTGAACGGCAACGACAACACCATCAAGGAGAAGCGCGAGCACATCGACCTGGACGACTTCTCCAAGTTC
GGCTGCGACAAGAACTCCGTGGACACCAACACCAAGGTGTGGGAGTGCAAGAAGCCCTACAAGCTGTCCACCAAGGACG
TGTGCGTGCCCCCCGCCGCCAGGAGCTGTGCCTGGGCAACATCGACCGCATCTACGACAAGAACCTGCTGATGATCAA
GGAGCACATCCTGGCCATCGCCATCTACGAGTCCCGCATCCTGAAGCGCAAGTACAAGAACAAGGACGACAAGGAGGTG
TGCAAGATCATCcagAAGACCTTCGCCGACATCCGCGACATCATCGGCGGCACCGACTACTGGAACGACCTGTCCAACC
GCAAGCTGGTGGGCAAGATCAACACCAACTCCAACTACGTGCACCGCAACAAGCAGAACGACAAGCTGTTCCGCGACGA
GTGGTGGAAGGTGATCAAGAAGGACGTGTGGAACGTGATCTCCTGGGTGTTCAAGGACAAGACCGTGTGCAAGGAGGAC
GACATCGAGAACATCCCCCAGTTCTTCCGCTGGTTCTCCGAGTGGGGCGACGACTACTGCCAGGACAAGACCAAGATGA
TCGAGACCCTGAAGGTGGAGTGCAAGGAGAAGCCCTGCGAGGACGACAACTGCAAGCGCAAGTGCAACTCCTACAAGGA
GTGGATCTCCAAGAAGAAGGAGGAGTACAACAAGCAGGCCAAGCAGTACCAGGAGTACCAGAACGGCAACAACTACAAG
ATGTACTCCGAGTTCAAGTCCATCAAGCCCGAGGTGTACCTGAAGAAGTACTCCGAGAAGTGCTCCAACCTGAACTTCG
AGGACGAGTTCAAGGAGGAGCTGCACTCCGACTACAAGAACAAGTGCACCATGTGCCCCGAGGTGAAGGACGTGCCCAT
CTCCATCATCCGCAACAACGAGCAGACCTCC
```

Figure 8

GRQTSSNNEVLSNCREKRKGMKWDCKKKNDRSNYVCIPDRRIQLCIVNLAIIKTYTKETMKDHFIEASKKESQLLLKKN
DNKYNSKFCNDLKNSFLDYGHLAMGNDMDFGGYSTKAENKIQEVFKGAHGEISEHKIKNFRKKWWNEFREKLWEAMLSE
HKNNINNCKNIPQEELQITQWIKEWHGEFLLERDNRAKLPKSKCKNNALYEACEKECIDPCMKYRDWIIRSKFEWHTLS
KEYETQKVPKENAENYLIKISENKNDAKVSLLLNNCDAEYSKYCDCKHTTTLVKSVLNGNDNTIKEKREHIDLDDFSKF
GCDKNSVDTNTKVWECKKPYKLSTKDVCVPPRRQELCLGNIDRIYDKNLLMIKEHILAIAIYESRILKRKYKNKDDKEV
CKIIQKTFADIRDIIGGTDYWNDLSNRKLVGKINTNSNYVHRNKQNDKLFRDEWWKVIKKDVWNVISWVFKDKTVCKED
DIENIPQFFRWFSEWGDDYCQDKTKMIETLKVECKEKPCEDDNCKRKCNSYKEWISKKKEEYNKQAKQYQEYQKGNNYK
MYSEFKSIKPEVYLKKYSEKCSNLNFEDEFKEELHSDYKNKCTMCPEVKDVPISIIRNNEQTS

Figure 9

SYNTHETIC GENES FOR MALARIAL PROTEINS AND METHODS OF USE

CROSS-REFERENCE TO RELATED APPLICATIONS

This application claims the benefit of U.S. Provisional Patent Application Ser. No. 60/345,051, filed Nov. 9, 2001.

The U.S. Government has rights in this invention arising out of National Institutes of Health (NIAID) Advanced Technology Small Business Innovative Research Grant number AI-46209.

FIELD OF INVENTION

The present invention relates to the fields of genetics and immunology and, more specifically, relates to compositions and methods for use of synthetic genes encoding the proteins of malaria pathogens. In particular, the invention pertains to the synthetic genes encoding malaria erythrocyte-binding proteins and their use in anti-malaria vaccines.

BACKGROUND OF THE INVENTION

Malaria is the world's most serious tropical disease that currently kills more people than any other communicable disease except tuberculosis. Approximately 41% of the world's population is at risk, and each year there are an estimated 300 million to 500 million clinical cases of malaria. Worldwide, approximately two million deaths per year can be attributed to malaria, half of these in children under five years of age. While the area affected by the endemic malaria has been steadily shrinking during the second half of the twentieth century, as reported by the World Health Organization, the control of the disease is becoming increasingly difficult. Increase in changes in land use linked to activities like road building, mining and irrigation projects, as well as the disintegration of health services, armed conflicts and resulting mass movements of refugees, population and economical pressures that displace people from rural to urban areas, effects of "global warming" and other climatic changes, all contribute to the spread of malaria. The disease is even reappearing in areas where it was previous under control or eradicated. The unprecedented increase of mobility in the recent years, including the rise of the affordable international travel, is also an important contributing factor in the recent re-emergence of the disease. "Imported" cases of malaria are now more frequently registered in developed countries. The United Kingdom, for example, registered 2364 cases of malaria in 1997, all of them imported by travelers. The emergence of multi-drug resistant strains of parasite is exacerbating the situation. New methods of fighting the disease that preferably would not contribute to the rise of drug-resistant forms of malaria are needed more than ever.

Malaria is caused by protozoa in the genus *Plasmodium*. Four species cause human malaria: *P. vivax, P. malariae, P. ovale,* and, the most deadly, *P. falciparum.* The *Plasmodium* pathogens, or sporozoites, are generally transmitted between humans by mosquitoes but can also occur by direct inoculation of infected blood, needles, or congenitally. Once the sporozoites enter the bloodstream of the human, they localize in liver cells. One to two weeks later, the infected liver cells rupture and release mature pathogens, or merozoites. The merozoites then begin the erythrocytic phase of malaria by attaching to and invading erythrocytes.

For invasion of the erythrocytes, malaria parasite *Plasmodium* uses erythrocytic receptors. *P. falciparum* invades erythrocytes through a 175 kDa erythrocyte binding protein named EBA-175 (Sim, B. K. L. 1995). EBA-175 functions as an invasion ligand that binds to its receptor, glycophorin A (Camus and Hadley, 1985; Sim et al., 1990; Orlandi et al., 1992; Sim et al., 1994b). Aotus monkeys immunized against RII by a DNA prime/protein boost approach control blood-stage challenge infection (Johes et al., 2001). EBA-175 belongs to the family of *Plasmodium* erythrocyte-binding proteins that also include *P. vivax* and *P. knowlesi* Duffy binding proteins. The receptor-binding domain found in each of these proteins lies in a conserved N-terminal cysteine-rich region II (RII).

Symptoms of the disease include high fever, chills, headaches, anemia and splenomegaly. Malaria is particularly dangerous to children (malaria is one of the five major causes of under-five child mortality) and pregnant women. It causes severe anemia, and is a major factor contributing to maternal deaths in malaria endemic regions. Pregnant mothers who have malaria and are HIV-positive are more likely to pass on their HIV status to their unborn child. Early diagnosis and prompt treatment of this stage of malaria is fundamental to malaria treatment and control.

Presently, there is a limited number of drugs for treatment of malaria. In many countries, most cases of malaria are diagnosed and treated in the home or by private sector practitioners, often incompletely and with irrational regimens. This speeds up the spread of parasite resistance to anti-malarial drugs. Due to this problem, a dramatic rise in the cost of treating uncomplicated malaria has been seen in some parts of the world. Therefore, there is a dire need for new methods of treating and preventing malaria. There is a particularly urgent need for a cost-effective vaccine capable of being incorporated into appropriate health delivery programs and of providing a sufficient duration of immunity.

Standard vaccines vary in the kind and duration of security that they provide. Those based on killed pathogens or antigens isolated from disease-causing agents cannot make their way into cells. Such responses are ineffective against microorganisms that invade cells such as the malarial pathogens. Those vaccines based on living matter, usually viruses, can enter cells to create the immune responses. However, live vaccines have complications of their own, such as causing full-blown illness in some people, or mutating to restore virulence.

Vaccines created from genetic material (Gurunathan et al., 2000) are naked polynucleotides that are used to vaccinate vertebrates. Genetic vaccines hold distinct advantages over their traditional counterparts. The best-studied structures consist of plasmids, which are small rings of double-stranded DNA derived from bacteria. Plasmids used for immunization have been altered to carry genes specifying one or more antigenic proteins normally made by the selected pathogen. At the same time, they do not include the genes that would enable the pathogen to reconstitute itself and cause disease.

The first generation of anti-malaria DNA vaccines did not induce optimal protective responses. A DNA vaccine encoding antigens expressed in either pre-erythrocytic or erythrocytic stages of the malarial pathogen has protected murine models from challenge with infective sporozoites (Sedegah et al., 1994; Doolan et al., 1996; Becker et al., 1998), but the protection was incomplete. Immunization of human volunteers with a DNA plasmid encoding the major coat protein of the sporozoite, the circumsporozoite protein of *P. falciparum*, induced antigen-specific cytotoxic T cell responses, but failed to induce antibody response. (Wang et al., 1998). Poor expression of the *Plasmodium* proteins from the plasmids in the mammalian host may be the cause of the suboptimal immune response in the mammalian host. The differences of codon usage between the protozoan *Plasmodium* and mammals are likely to underline the low levels of protein expression.

It is known that codon usage varies considerably between species (Ikemura, 1985). Each amino acid, with the exception of methionine and tryptophan, can be encoded by two to six different synonymous codons. The frequencies at which these synonymous codons are used depends on the level of protein expression and differ among organisms. In general, highly expressed genes are biased towards codons that are recognized by the most abundant tRNA species in the organism (Ikemura, 1985). For instance, the A+T content in the genome of the *P. falciparum* is 80% as compared to 45% in humans.

One measure of the bias is the codon adaptation index ("CAI"), which measures the extent to which the codons used to encode each amino acid in a particular gene are those which occur most frequently in a reference set of highly expressed genes from an organism (Sharp and Li, 1987). As the native sequences of *Plasmodium* genes have very low CAIs in mammalian cells, the expression of these native sequences from the vaccine vectors is suboptimal. As a result, the anti-malaria DNA vaccines fail to induce the immune response necessary for the full protection from malaria.

Therefore, it is clear that there is an exceptionally strong need for an anti-malaria vaccine capable of inducing a full-scale immune response. A DNA vaccine capable of high levels of expression of a *Plasmodium* erythrocyte-binding protein sequence in a mammalian host would prevent the entry of the *Plasmodium* pathogen into the erythrocytes. Therefore, such vaccine would be highly useful for prevention and treatment of malaria in all settings. Thus, synthetic gene sequences for *Plasmodium* erythrocyte-binding proteins that could be incorporated into anti-malaria DNA vaccines are a highly useful tool for the production and development of such vaccines. Furthermore, the compositions and methods of production and use of such DNA vaccines, whose pathogenic codons have been modified to resemble codon usage of an infected host, would be highly useful for combating malaria. The methods of modification of the gene segments and production of DNA sequences of the malaria pathogen erythrocyte-binding protein in order to increase protein expression and, thus, increase antibody responses in DNA-vaccinated organisms would also be extremely valuable for fighting the disease.

The vaccination regimes where a DNA immunization ("prime") is followed by the administration of the corresponding protein ("boost") may be even more effective in induction of the full-scale stable anti-malarial immune response. Large-scale production methods of malarial proteins are necessary for such DNA prime/protein boost regimens. Synthetic genes encoding malarial proteins that are optimized to match the codon usage of the expression host are useful for such large-scale protein production. Malaria protein EBA-175, especially its RII domain, and synthetic genes encoding it are particularly important in the development of anti-malaria vaccines and vaccination regimens.

Also important for anti-malaria vaccination and treatment of malaria is analysis of the properties of the recombinant malarial proteins expressed in different systems. There are important differences in the protein expression mechanisms between the malaria pathogens and other organisms, such as yeast or mammals. As a result, when malarial proteins are expressed in the non-native environment, they may possess different properties from the indigenous malarial proteins, which may affect the recombinant proteins' immunogenic activity. Of a particular concern are the differences in the N-glycosylation of proteins: a post-translational attachment of sugars to the amino group of the amino acid asparagines (Asn). This post-translational modification is common in many organisms, including mammals and yeast, but does not occur in malaria pathogens. N-glycosylation can grossly affect protein properties, including their immunogenicity. Synthetic genes that can be manipulated to affect the properties of the encoded polypeptides, including their glycosylation patterns in different organisms, are very useful for the analysis of the differences of such properties and for designing optimal anti-malaria vaccines and vaccination regimens.

SUMMARY OF THE INVENTION

Compositions of synthetic gene sequences of a malaria pathogen are described herein. More specifically, the synthetic gene sequences encode amino acid sequence of erythrocyte-binding protein of a malaria pathogen *Plasmodium falciparum* (*P. falciparum*). The preferred erythrocyte-binding protein amino acid sequences is the sequence encoding receptor-binding domain (RII). Even more specifically, the synthetic gene sequences encode the RII region of the *P. falciparum* EBA-175 protein (SEQ ID NO:2). The synthetic gene sequences are designed to maximize protein expression of the encoded protein in a mammalian host, wherein the codon composition of the synthetic gene sequence is designed to approximate the codon composition of the host organism. The present invention describes the methods of making and producing such synthetic gene sequences.

In one embodiment of the present invention, these synthetic gene sequences are useful for the production of anti-malaria DNA vaccines of improved immunogenicity. The DNA vaccine expression vectors that contain synthetic genes for erythrocyte-binding protein are described. Administrations of such vaccines to a mammal, including a human, with the purpose of inducing immunity against malaria pathogen allows for reduced vaccine doses and elicits reliable immune response in the host. The present invention also describes the methods of eliciting immune response to malaria pathogen in a mammalian host using the synthetic gene sequence encoding a receptor-binding fragment of the erythrocyte-binding protein.

In other embodiment of the present invention, the synthetic gene sequences are useful for production of malaria erythrocyte-binding protein in the yeast *Pichia pastoris*. The *Pichia pastoris* expression vectors for production of the recombinant erythrocyte-binding proteins are described. The robust method of large-scale production of the recombinant erythrocyte-binding protein and means of optimization of such method are also provided. The recombinantly produced protein is useful for inducing anti-malaria immune response when administered to mammals, in particular as a part of certain vaccination regimes.

In the other embodiment of the present invention the synthetic gene sequences are altered to affect the properties of the encoded erythrocyte-binding protein. In particular, the amino acid sequences that control N-glycosylation of the protein during expression in some organisms are mutated. *Pichia pastoris* and mammalian expression vectors encoding such altered synthetic gene sequences are described. The proteins expressed from such vectors are not N-glycosylated. The comparison of the N-glycosylated and non-N- glycosylated malaria proteins encoded by synthetic genes, especially their immunogenic properties when administered in the form of a purified protein or a DNA vaccine to a mammal, is useful for the development of improved anti-malaria vaccines and vaccination regimens.

BRIEF DESCRIPTION OF THE FIGURES

FIG. 1 Panel A is a scheme of gene structure of EBA-175 showing region II (RII) and division of six other regions. Panel B is a film showing the chemiluminescence-detected levels of protein expression in human melanoma cells transfected with varying quantities of plasmids expressing native or synthetic region II of EBA-175

FIG. 3 is a scheme showing fermentation optimization of RII at 2L scale. Panel A is a scheme of optimization strategy. Panel B is the bar graph showing the concentration of RII protein for the 72 hours post-induction time points under different induction conditions. RII protein concentration in the supernatants were determined by cation exchange HPLC (high performance liquid chromatography). The conditions for the glycerol batch phase were maintained constant (30° C., pH 5.0, dissolved oxygen (DO) 40%). The condition being optimized was adapted at the methanol-fed induction phase.

FIG. 4 is a scheme of the RII protein purification process (Panel A) and the purity of the final purified RII protein produced in 60-L fermentation (Panels B and C). Supernatant from the 60-L fermentation harvest (72 h) was used. The purity of RII protein is >95% as shown by Coomassie stained SDS-PAGE gel (Panel B) and by reverse phase HPLC under non-reduced conditions (Panel C).

FIG. 5 is a scheme of EBA-175 gene with the N-glycosylation sites marked by asterisks (*). Lower panel shows amino acid sequence of putative N-glycosylation sites within native EBA-175 and position of conservative mutations within the *P. pastoris* expressed non-N-glycosylated RII protein.

FIG. 6 is EBA-175 RII synthetic gene nucleotide sequence with N-glycosylation sites.

FIG. 7 is EBA-175 RII deduced amino acid sequence with N-glycosylation sites

FIG. 8 is EBA-175 RII synthetic gene sequence without N-glycosylation sites

FIG. 9 is EBA-175 RII deduced amino acid sequence without N-glycosylation sites

DETAILED DESCRIPTION

Figure 2:
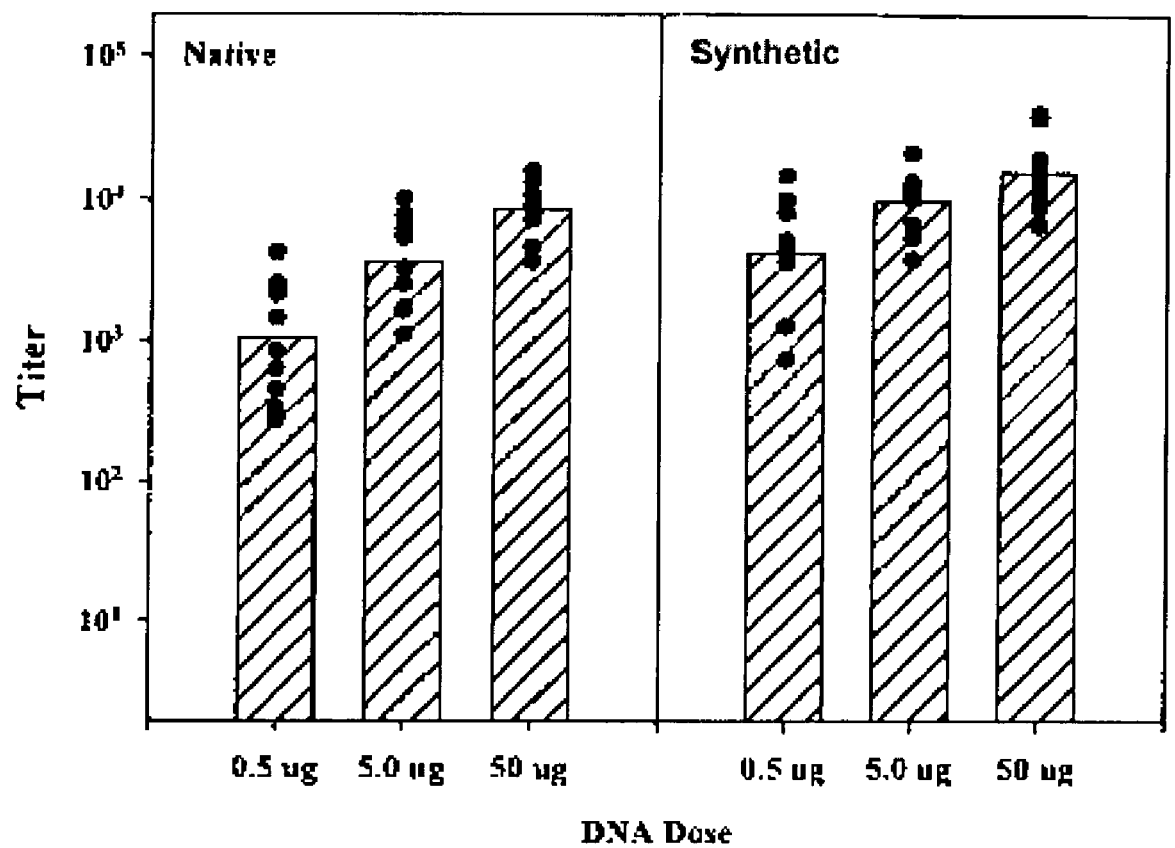
FIG. 2 is a bar graph showing the levels of antibody titers measured by enzyme-linked immunosorbent assay (ELISA) in outbred mice immunized with DNA vaccines expressing native or synthetic EBA-175 RII. ELISA results are reported as the interpolated reciprocal dilution estimated to give an optical density of 0.5. Bars represent the geometric mean titers and the solid circles represent individual responses.

Synthetic gene sequences encoding malaria pathogen erythrocyte-binding protein (EBP) and methods of producing of such synthetic gene sequences are provided. Compositions and methods of eliciting immune response to the protein encoded by the synthetic gene sequences are also provided. Methods of large-scale production of the malaria pathogen erythrocyte-binding protein encoded by synthetic gene sequences are described. Methods of modification of the EBP synthetic gene sequences to alter the properties of the resulting protein are also provided, along with the synthetic gene sequences and expression vectors for such altered EBP. These compositions and methods can be used for treating and preventing malarial diseases and infection.

As used herein, the term "synthetic" is defined to mean laboratory produced in a manner known to one skilled in the art. The term "gene segment" and "gene sequence" are used interchangeably and are defined to mean a portion of a nucleotide sequence that transcribes RNA, either m, r, or t, used in the production of polypeptides or used directly. The term "isolated" refers to a composition that is substantially or essentially free from at least some of the components that normally accompany it in its native state. Thus, the isolated proteins of this invention do not contain some of the materials normally associated with their in situ environment. Typically, the isolated proteins of the invention are at least about 80% pure, usually at least 90% pure and preferably at least 95% pure as measured by band intensity on a Coomassie-stained gel. The term "host" is defined to mean an organism that can be infected by a pathogen, and the term "pathogen" is defined to mean any organism that causes a deviation in a normal state. The term "ligand" is defined to mean a molecule that will bind to a complementary site on a given structure. The term "codon" is defined to mean the nucleotide triplet that specifies the amino acid to be inserted in a specific position in a forming polypeptide during translation. The term "altered" is used interchangeably with the term "mutated" to refer to the changes in the nucleotide sequence. The term "improved immunogenicity" is defined herein as the following two characteristics possessed, separately or together, by a vaccine: (a) the ability of a vaccine to induce, at any single dose, higher antibody titers than a reference vaccine; (b) the ability of a vaccine to induce antibody titers comparable to that of a reference vaccine, wherein the administered dose of the vaccine of "improved immunogenicity" is reduced 10 or more fold compared to the dose of the reference vaccine.

The term "sequence homology" is also known in the art as "sequence similarity" between two or more sequences. A high degree of "sequence homology" is at least approximately 60% amino acid similarity between the two amino acid sequences. "Sequence similarity" can be determined by a number of commercially available or freeware programs which are widely used in the art. Examples of such programs are available from the World Wide Web (WWW) "Sequence Analysis Tools" server of National Institutes of Health (NIH) in the United States of America (Bethesda, Md.).

They are also available from the WWW server of Institut Suisse de Bioinformatique (ISB) "ExPASy Proteomic Tools" in Switzerland.

The term "large-scale protein production" is used to refer to the production of proteins by a method such as liquid fermentation on a scale over one liter.

Additionally, the terms "a", "an" and "the" as used herein are defined to mean "one or more" and include the plural unless the context is inappropriate. The terms "polypeptide", "peptide" and "protein", as used herein, are interchangeable and are defined to mean a biomolecule composed of two or more amino acids linked by a peptide bond.

According to the present invention, a synthetic gene segment of a synthetic nucleotide sequence encodes an amino acid sequence of erythrocyte-binding protein of a malaria pathogen. In the preferred embodiment of the present invention, the erythrocyte-binding protein is of a malarial pathogen *Plasmodium falciparum*. In particular, the present invention describes the synthetic gene segment encoding the amino acid sequence of the 616 amino acids of the receptor-binding domain (RII) of the *P. falciparum* EBA-175 as described in Sim, et al. (1994) and incorporated herein by reference. The 5' cysteine-rich region of the protein, designated region II ("RII"), was chosen for synthesis because it binds to its receptor—sialic acids on glycophorin A—for invasion of erythrocytes by the malarial pathogen, as described in Narum, et al (2000) and incorporated herein by reference. The scheme of the gene structure of the EBA-175 is shown in FIG. 1, panel A. The region RII was chosen because antibodies directed against RII block invasion of *P. falciparum* strains, which have the capability to invade erythrocytes by distinct pathways, as described in Narum, et al (2000). The use of this particular receptor-binding protein from this particular malaria pathogen is for illustration purposes only and it should be understood that any pathogen ligand capable of invading a host's cell by distinct pathways may be substituted. The ligands include, but are not limited to, *P. vivax* and *P. knowlesi* Duffy binding proteins, particularly their receptor-binding (RII) regions, and any malaria pathogen protein containing sequences highly similar to RII region.

Methods commonly known or used in the art can be used to identify the sequences of the malaria pathogen ligands for the production of synthetic genes. One exemplary method is to utilize similarity searches of the malaria pathogen sequences. Searchable databases of *Plasmodium* genomes, such as the *Plasmodium falciparum* genome database internet server at TIGR Institute, are becoming readily available.

Once the receptor-binding protein is selected from a desired malaria pathogen, a host species is selected from a group that can be infected by the pathogen. In the most preferred embodiment of the present invention, the host species is *Homo sapiens* (humans).

The present invention includes a method of producing a synthetic gene segment of a malaria pathogen erythrocyte-binding ligand. The codon usage of highly expressed genes in the host is compared to that of the selected pathogen genes. This comparison can be performed, for example, with the help of the CodonW software by John Peden, available as freeware from the internet. The most frequently used codons for encoding a particular amino acid of the host are used to synthesize a gene segment encoding the receptor-binding protein. The method involves identifying nucleotide sequence of a native gene segment from a pathogen that encodes for a desired erythrocyte-binding ligand, comparing the codons most frequently used by the malaria pathogen and the host, designing the synthetic gene sequence by substituting the nucleotides in the native malaria pathogen gene to approximate the codon composition of the mammalian host, and synthesizing a synthetic gene sequence. One skilled in the art could produce a synthetic gene by obtaining the long oligomers through a commercial source, anneal them together to form a double strand and then connect them in the proper sequence, as described generally in the manuals common in the art, such as Sambrook, J., et al., 2000, which is incorporated herein by reference in its entirety. Protein expression elicited from a synthetic sequence can be tested in vitro and in vivo using those methods known and used in the art.

A synthetic gene segment, as described herein, is useful in the production of DNA vaccines, protein vaccines, and therapeutic compositions. As used herein, the term "DNA vaccine" includes compositions comprising a synthetic gene sequence of the present invention and which is used for immunization of individuals prior to or following infection of a malarial pathogen. As used herein "protein vaccines" includes compositions comprising a protein encoded by a synthetic gene sequence of the present invention and is used for immunization of individuals prior to or following infection of a malarial protein. Accordingly, the present invention includes DNA and protein vaccines that inhibit binding of an EBA-175 protein to an erythrocyte. Additionally included in the present invention are DNA and protein vaccines that inhibit malarial invasion into an erythrocyte.

The present invention includes a method for producing a DNA vaccine comprising a synthesized gene sequence as described above. A synthetic gene sequence is cloned into a vector using molecular biology techniques that are known and used in the art, and described generally in the manuals common in the art, such as Sambrook, et al. (2000). In a preferred embodiment, the vector is a DNA vaccine vector. Standard techniques of molecular biology known and used in the art for preparing and purifying DNA constructs enable the preparation of the DNA vaccines of this invention. While standard techniques of molecular biology are therefore sufficient for the production of the products of this invention, the specific constructs disclosed herein provide novel synthetic gene segments.

In other embodiment of the present invention the synthetic gene sequences are used for production of malaria erythrocyte-binding protein. In a preferred embodiment of the present invention, the synthetic gene sequences are introduced into the expression vectors for the yeast *Pichia pastoris*. *Pichia pastoris* expression vectors for production of the recombinant erythrocyte-binding proteins encoded by the synthetic gene sequences are described. Using procedures common in the art, the *Pichia pastoris* expression vectors are introduced into an appropriate strain of *Pichia pastoris*. The method of expression of erythrocyte-binding protein in *Pichia pastoris* is optimized according to a procedure provided herein, which is useful for robust large-scale production of the recombinant erythrocyte-binding protein. The present invention encompasses a method for large-scale production, including expression and purification, of the erythrocyte-binding protein. This large-scale production can be used to produce clinical grade material to administer to humans for prevention and treatment of malaria, including, but not limited to as protein vaccines or as a part of the DNA prime/protein boost immunization regimens. Such immunization regimens with the RII protein have been shown to protect Aotus monkeys from malaria in pre-clinical trials.

Other uses of the recombinant malaria-binding proteins encoded by the synthetic gene sequences are contemplated herein. One such use for raising the antibodies or serum for administration to animals or humans with the purpose of passive immunization and treatment of malarial disease.

In another embodiment of the present invention, the synthetic gene sequences encoding EBA-175 RII protein are altered to affect the properties of the encoded erythrocyte-binding protein. In the preferred embodiment of the present invention the amino acid sequences that determine the attachment of polysaccharides ("glycosylation") to the polypeptide chain are replaced with the amino acids with similar properties ("conserved substitution") except for the ability to guide glycosylation. In particular, N-glycosylation sites in the synthetic gene of the EBA-175 RII region are altered. *Pichia pastoris* and mammalian expression vectors encoding such altered synthetic gene sequences are described. The altered EBA-175 RII protein is expressed in both *P. pastoris* and mammalian cells and compared to the non-altered protein encoded by the non-mutated synthetic gene sequence. The altered EBA-175 RII proteins are not N-glycosylated either in *P. pastoris* or mammalian expression system.

In the preferred embodiment of the present invention, the properties of the non-N-glycosylated RII EBA protein are tested. In the most preferred embodiment, the erythrocyte-binding properties, the ability to inhibit the growth of malaria parasite, and, in particular, the immunogenic properties of the non-glycosylated protein were tested. The immune response induced by administration of the non-N-glycosylated protein to the mammals was tested. The immune response induced by the administration of DNA vaccine encoding the non-glycosylated protein to the mammals was also tested. The comparison of the properties of the N-glycosylated and non-N-glycosylated malaria proteins encoded by synthetic genes, especially their immunogenic properties resulted in the understanding that N-glycosylation of the EBP protein does not affect its properties important for its use in the anti-malaria vaccine compositions and vaccination methods. Therefore, a foremost concern in the development of anti-malaria vaccine methods and compositions was eliminated.

The present invention includes a method of inducing an immune response to a pathogen by administering an amount of a synthetic gene segment or a protein encoded by the synthetic gene segment, or a combination of both, to a potential host in a sufficient amount to induce an immune response. In a preferred embodiment the pathogen is a malarial pathogen namely a species of *Plasmodium*. In a further embodiment, the species of *Plasmodium* is *falciparum*. In a still further embodiment of the present invention, the potential host is a mammal, namely a human. Also included in the present invention is a method of treating malaria. This embodiment of the invention requires selecting an infected host and administering a sufficient dosage of a synthetic gene segment or a protein encoded by the synthetic gene, or a combination of both, to inhibit the malarial pathogen.

In a preferred embodiment, a DNA or protein vaccine for passive or active immunization against malaria is combined with a pharmaceutically acceptable carrier to facilitate administration. The preferred dose for human administration of the DNA vaccine is $10^2$ to $10^4$ $TCID_{50}$/person. (TCID is an abbreviation for tissue culture infectious doses). The preferred dose for human administration of the protein vaccine for active or passive immunization is from 0.001 mg/kg to 10 mg/kg. The dose should be adjusted to suit the individual to whom the composition is administered and will vary with certain factors such as age, weight and metabolism of the individual. The vaccines may additionally contain stabilizers or physiologically acceptable preservatives.

The vaccine can be administered by any appropriate route, including but not limited to, orally, parenterally, intravenously, intradermally, intramuscularly, subcutaneously, or topically, in liquid or solid form, in a single dose or a dose repeated after a certain time interval. The vaccine may be provided to the physician in a lyophilized form, reconstituted in an appropriate solvent such as deionized water or saline and administered as a single injection or a series of injection at a time intervals necessary for the achievement of the immune response or treatment of the disease. The different variations of vaccines may be combined in a single dose or a vaccination regimen to achieve the desired anti-malarial effect.

Preferably, the administration of the DNA vaccine will result in in vivo protein expression of the proteins encoded by the open reading frames contained in the expression vector construct. Most preferably, the administration of the DNA vaccine will result in the induction of immunity against the erythrocyte binding proteins, which are encoded by the synthetic genes incorporated into the vaccine. Preferably, the administration of the protein vaccine will result in induction in the host of the immunity of the protein component of the vaccine. Preferably, the administration of the antibody vaccine will result acquisition by the host of immunity against the malarial disease.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Analysis of Codon Usage

The most commonly used codons for *H. sapien* and *P. falciparum* were determined from a Codon Usage Tabulated from Genbank (CUTG) website. Codon Adaptation Indices were calculated using the CodonW software by John Peden, available as a freeware, with a user-defined set of codon relative adaptiveness values (Wcodon) based on codon usage in a compendium of highly expressed human genes as described in the teaching by Haas, et al., 1996, which is incorporated herein by reference in its entirety.

EXAMPLE 2

Codon Optimization

Codon-optimized gene fragments encoding EBA-175 RII were constructed in order to test the hypothesis that codon optimization would improve the expression and immunogenicity of malaria DNA vaccine plasmids. Table 1 shows the differences between the most frequently used codons in the *P. falciparum* genes and in highly expressed human genes. For every amino acid, which can be encoded for by more than one codon, the most frequently used codon in *P. falciparum* is different from that used in humans. Approximately one in three nucleotides was changed to optimize the sequences, and the G+C content was raised from approximately 26% to approximately 56% in the optimized sequences as shown in Table 2. The CAI of the codon optimized pSRII and pSMSP1$_{42}$ genes was increased from <0.28 to ≧0.98 (maximum possible value 1.0).

TABLE 1

Comparison of most abundant codon for each amino acid used by malaria parasite (*Plasmodium falciparum*) and highly expressed human genes (*Homo sapiens*).

| Amino acid | Plasmodium falciparum | Homo sapiens | Amino Acid | Plasmodium falciparum | Homo sapiens |
|---|---|---|---|---|---|
| A | GCA | GCC | L | UUA | CUG |
| R | AGA | CGC | K | AAA | AAG |
| N | AAU | AAC | M* | AUG | AUG |
| D | GAU | GAC | F | UUU | UUC |
| C | UGU | UGC | P | CCA | CCC |
| Q | CAA | CAG | S | AGU | AGC |
| E | GAA | GAG | T | ACA | ACC |
| G | GGU | GGC | W* | UGG | UGG |
| H | CAU | CAC | Y | UAU | UAC |
| I | AUU | AUC | V | GUA | GUG |

*These amino acids are encoded by single codons.

TABLE 2

Comparison of native and optimized vaccine candidate sequences.

| Gene | Number of native nucleotides altered/total (%) | G + C content (%) native/optimized | Codon adaptation index (CAI) native/optimized |
|---|---|---|---|
| EBA-175 RE | 591/1848 (32.0) | 27.3/56.7 | 0.276/0.988 |

EXAMPLE 3

DNA Vaccine Construction

The DNA vaccine containing the native gene fragment for EBA-175 RII has been previously described by Sim, et al, 1995, incorporated herein in its entirety by reference. Synthetic DNA sequences encoding the 616 amino acids of EBA-175 RII (3D7 strain) were designed by reverse translation of the amino acid sequence using DNAStar Lasergene99 (DNAStar, Inc. Madison, Wis.). The reverse translation used the most abundant codon for each amino acid found in a compendium of highly expressed human genes, except for S (serine), which was reverse translated as UCC rather than AGC (the two codons are used at approximately equal frequency in highly expressed human genes). Within the back-translations encoding RII, BamHI restriction enzyme sites were removed by changing individual nucleotides without altering the amino acid sequence. The RII gene (SEQ ID NO:1) was synthesized by Operon Technologies, Inc (Alameda, Calif.). The synthetic RII gene was amplified by PCR and cloned into the DNA vaccine plasmid VR1020 as described in Luke, et al, 1997.

The synthetic gene segment encoding RII was PCR-amplified using the following primers:

```
sense
5'ATCGGGATCCGGCCCAACACCTCCTCC3'     (SEQ ID NO:6)

antisense
5'ATCGGGATCCTCAGGAGGTCTCTCGTTGTT3'  (SEQ ID NO:7)
``` and directly cloned into a BglII restriction site in plasmid VR1020 obtained from Vical, Inc. (San Diego, Calif.). The DNA sequence of the junction site of the inserted gene or the complete insert was determined to ensure that an open reading frame was maintained. EBA-175 plasmid vaccines were purified as described in Sim, et al, 2001, incorporated herein in its entirety by reference.

EXAMPLE 4

In Vitro Transfection Studies

Human melanoma cells (UM499) were transiently transfected with plasmids separately with Lipofectamine® transfection reagent following the manufacturer's suggestions (Life Technologies, Gaithersburg, Md.). Recombinant RII that was secreted into culture supernatant was detected and quantitated as a chemiluminescent signal by using a specific RII monoclonal antibody R217 and a commercially obtained chemiluminescence-linked western blot kit (Western-Light® western blot kit, Topix, Bedford, Md.) according to the manufacturer's protocol. Chemiluminescent signals were detected by exposure of the processed membrane to autoradiographic film (Hyperfilm-ECL® autoradiographic film, Amersham Life Sciences, Inc., Cleveland, Ohio). Quantitation of ECL Western blots were performed on a Molecular Imager FX (BioRad, Hercules, Calif.) and units of intensity were reported as counts per square mm.

EXAMPLE 5

In vitro Protein Expression

FIG. 1, panel B, shows the levels of in vitro protein expression from DNA vaccine plasmids: pNRII and pSRII. The comparison of the protein expression levels revealed that levels from optimized codon gene fragments were greater than levels from native genes. The results indicated that 0.125 μg codon-optimized plasmid pSRII expressed comparable amounts of protein to 1 μg of non-optimized plasmid pNRII. Quantitating RII expression by correlating the levels of RII protein with band intensities demonstrated that 0.125 and 0.25 μg pSRII expressed 1919 and 4361 counts/mm$^2$, respectively compared to 1 μg pNRII that expressed an average of 3298 counts/mm$^2$ for the duplicate samples. This represents a 4–8 fold increase in protein expression. RII protein produced in in vitro transfection experiments was recognized by RII-specific growth inhibitory monoclonal antibody R217 that recognizes reduction sensitive epitopes. This proves that the proteins encoded by the vaccine plasmids are properly folded.

EXAMPLE 6

Animals, Immunizations, and Antibody Assays

Groups of outbred ICR (Harlan Sprague Dawley, Inc., Indianapolis, Ind.) or CD1 (Charles River, Raleigh, N.C.) mice were inoculated intradermally in the tail with 0.5, 5.0 and 50 μg of EBA-175 RII plasmids. Sera were assessed for RII-specific antibodies by ELISA and indirect immunofluorescent antibody test (IFAT) as described in Sim, et al, 2001, and Kumar, et al, 1986. ELISA results were reported as the interpolated reciprocal dilution estimated to give an optical density of 0.5. Group size was 10 ICR mice per group. FIG. 2 shows that at each dose of DNA tested, mice immunized with the synthetic gene sequence encoding RII had statistically significantly higher ELISA titers against recombinant RII than mice immunized with plasmids containing native RII (p=0.024, 0.003, 0.003, at 50, 5.0 and 0.5 μg doses, respectively, by two tailed t-test on log transformed titers). The geometric mean IFAT titer in sera from mice immunized with 0.5 μg pSRII was similar to that induced by 50.0 μg pNRII. Thus, the same antibody response was induced by 100-fold less of the plasmid expressing the codon optimized synthetic gene. Similar results were obtained against whole parasites in indirect fluorescent antibody test against parasite infected erythrocytes.

EXAMPLE 7

Pilot-Scale Production of Recombinant EBA-175 Region II In *Pichia pastoris*

Purified *P. pastoris* derived EBA-175 RII protein possesses the same erythrocyte-binding characteristics as native EBA-175. *Pichia* Expression Kit from Invitrogen (Carlsbad, Calif.) was used for cloning and expression of the synthetic RII gene optimized for codon usage. RII synthetic gene was cloned into the *Pichia pastoris* expression vector pPICZαA (catalog no. V195-20) and introduced into the *Pichia pastoris* host strain X-33 according to the manufacturer's instructions.

Fermentation parameters in a 2 L bioreactor, which included pH, temperature, biomass and methanol feed rates, where optimized as shown in FIG. 3. During fermentation, RII protein concentration in the supernatants was determined by cation exchange HPLC. The conditions for the glycerol batch phase were standard in the art and maintained constant at 30° C., pH 5.0, 40% dissolved oxygen (DO). The conditions at the methanol-fed induction phase were adapted in the order shown in FIG. 3, panel A. The methanol fed-batch phase was initiated at 200 g/L wet cell weight (WCW), methanol feed rate was 6 ml/L/h. PTM4 trace salts were added to the fermentation basal salts at the glycerol batch phase. Samples were collected every 24 hours. FIG. 3, panel B, shows the results of the fermentation at the 72 h post-induction time point. The optimal induction conditions were determined to be 24° C., pH6.0, 200 g/L WCW.

Fermentation parameters were also optimized for a 10 L bioreactor and the optimized parameters were applied to a 60 L pilot-scale fermentation run. Table 3 shows the results of the scaling up of the fermentation. At the induction phase, optimized bioreactor conditions (24° C., pH 6.0, 180 g/L WCW) and methanol feed rate of 7 ml/L/hr were used. RII protein titer in the crude supernatant was determined by reverse phase HPLC. RII was comprised of approximately 50% hyperglycosylated RII protein and approximately 15% cleavage products that are excluded from the weight of the final product. Fermentation was shown to be robust and easily scalable.

TABLE 3

Production and purification of recombinant EBA-175 RII in *P. pastoris*

| Fermentation scale (L)[1] | Region II Titer in fermentation supernatant (mg/ml)[2] | Region II recovery after purification (mg/ml) |
| --- | --- | --- |
| 10 | 675 | 100 |
| 60 | 827 | 150 |

*P. pastoris* expressed RII was purified from the fermentation broth using Expanded Bed Absorption technology and ion-exchange column chromatography according to the scheme shown in FIG. 4, panel A. The purity of the RII was >95% as determined by Coomassie stained sodium-dodecyl sulphate gel-electrophoresis (SDS-PAGE) and by reverse-phase HPLC under non-reduced conditions, as shown in FIG. 4, panels B and C. The yield post-purification was approximately 150 ml/L of fermentation supernatant. Full biochemical characterization of RII was performed as shown in Table 4.

TABLE 4

The order of biochemical characterization procedures for the recombinant RII protein expressed in *P. pastoris*.

Appearance
pH
Purity by reverse phase-HPLC
SDS-PAGE-Silver Stain
Strength by UV-Absorbance
Identity by reduced peptide map
Purity by bacterial endotoxin
Monosaccharide composition analysis
Biological Assay (erythrocyte binding)

Table 5 shows the analysis of N-linked glycosylation of the recombinant RII protein. Purified RII protein was further fractionated by cation exchange chromatography using a linear elution gradient with decreased slope and each of the resulting six fractions (F1–F6 in Table 5) was analyzed.

TABLE 5

Monosaccharide composition analysis of the purified RII protein

| | | Fractions of purified RII[2] | | | | | |
| --- | --- | --- | --- | --- | --- | --- | --- |
| Monosaccharide[1] | RII[2] | F1 | F2 | F3 | F4 | F5[3] | F6[3] |
| GlcN (nmole) | 2 | 4 | 4 | 2 | 2 | 2 | 0.8 |
| Man (nmole) | 16 | 31 | 32 | 16 | 17 | 11 | 6.5 |
| Number of sites (out of 5) that are N-glycosylated | 1 | 2 | 2 | 1 | 1 | <1 | <1 |

[1]Nanomoles of monosaccharide were normalized to 1 nmole of protein.
[2]Purified RII protein prior to fractionation.

The monosaccharide composition analysis of the recombinant RII protein indicated a heterogeneous population consisting of N-glycosylated and non N-glycosylated RII protein. Hydrolysis analysis of RII determined that of potential sites approximately 20% (or approximately 1:5 ratio of putative sites) were N-glycosylated. It was also determined that N-glycosylation consists of 0, 1, or 2 core units comprised of Man 14-16GlcNAc2.

The robustness of the fermentation and purification process at pilot scale provides the platform for process transfer to a GMP facility for manufacture of clinical-grade *P. pastoris*-expressed RII protein for use in human trials.

EXAMPLE 8

RII-Specific Antibodies Block EBA-175 Erythrocyte Binding

Anti-RII antibodies were raised in rabbits against *P. pastoris*-expressed RII by a DNA prime/recombinant protein boost vaccination regimen. These antibodies recognized malaria schizonts, which was determined by inmmunofluorescence assay (IFA), and blocked native EBA-175 erythrocyte binding, as shown in Table 6. Table 6 also shows that purified immunoglobulin (IgG) from immunized rabbits inhibited parasite growth in vitro. Growth inhibition (%) was determined for 3D7 strain of *P. falciparum* after 2 cycles of red blood cell (RBC) invasion using purified rabbit IgG at 0.5 mg/mL compared to control (empty vector/adjuvant alone). Inhibition was deemed statistically significant at P<0.05 using 2-tailed Students t-test.

TABLE 6

Anti-RII antibodies induced by DNA prime/*P. pastoris* recombinant protein boost block function of EBA-175.

| Rabbit No. | RII vaccine | Reciprocal IFA Titer | RII ELISA Titer[1] | Blocking Abs $IC_{50}$[2] | % growth inhibition |
|---|---|---|---|---|---|
| 54 | RII | 102,400 | 315,987 | 18,000 | 37 |
| 55 | DNA prime/ Protein boost | 102,400 | 282,712 | 10,000 | 41 |

[1]Interpolated reciprocal RII ELISA titers are reported for an optical density (OD) of 0.5
[2]Interpolated reciprocal serum concentration at which native [$^{35}$S] metabolically labeled EBA-175 red blood cell binding was blocked by 50%.

EXAMPLE 9

Expression of Glycosylated and Non-Glycosylated EBA-175 RII Protein in *Pichia pastoris*

*Plasmodium falciparum* EBA-175 RII protein contains five putative N-glycosylation sites as shown in the schematic EBA-175 gene structure in FIG. 5. However, N-glycosylation of proteins does not occur in the native EBA-175 host *P. falciparum*. On the other hand, several potential expression systems for the recombinant EBA-175 RII protein (baculovirus, *P. pastoris* and mammalian cells) have the capacity to N-glycosylated proteins. N-glycosylation of the recombinant protein in these systems may alter its immunogenicity. The result of the N-glycosylation analysis of the recombinant RII protein reported in Table 7 show that 20% of all *P. pastoris* expressed RII was N-glycosylated with $MAN_{14-16}GlcNAc_2$. The other 80% of the putative sites were left non-N-glycosylated, which means that 1 in 5 of the putative glycosylation sites are occupied when RII is expressed in *P. pastoris*.

TABLE 7

Analysis of N-lined glycosylation of *P. pastoris* expressed RII

| | Monosaccharide Composition Analysis of RII[1] | |
|---|---|---|
| | GlcN (nmole) | Man (nmole) |
| Average (% SD) | 1.71 (1.22) | 14.27 (4.62) |
| Normalized | 2 | 16 |

[1]Nanomoles of monosaccharide were normalized to 1 nmole of protein.

Figure 10:
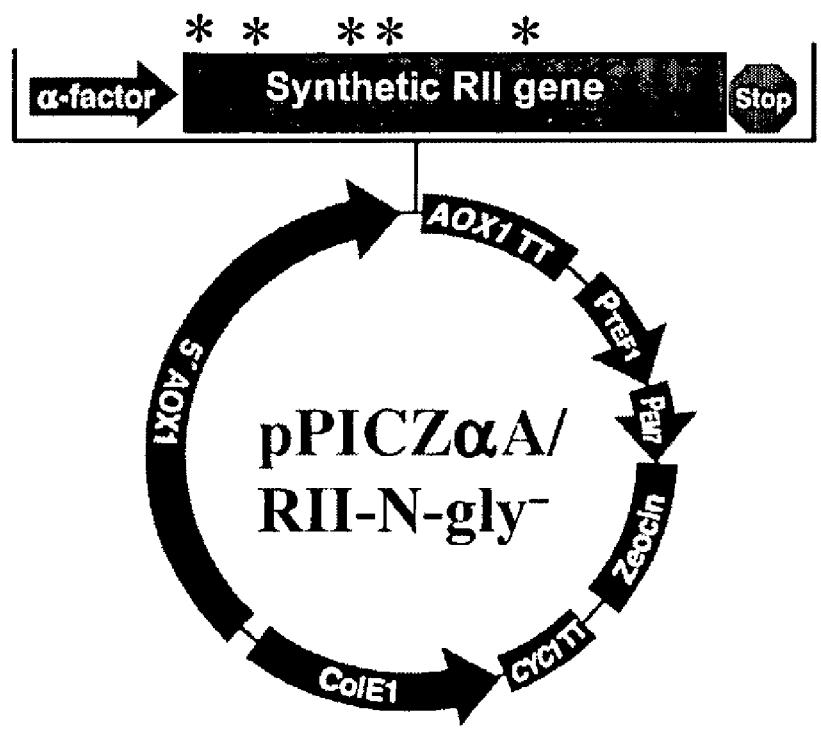
FIG. 10 is a scheme of the *P. pastoris* expression vector for expression of EBA-17 5RII.
Figure 11:
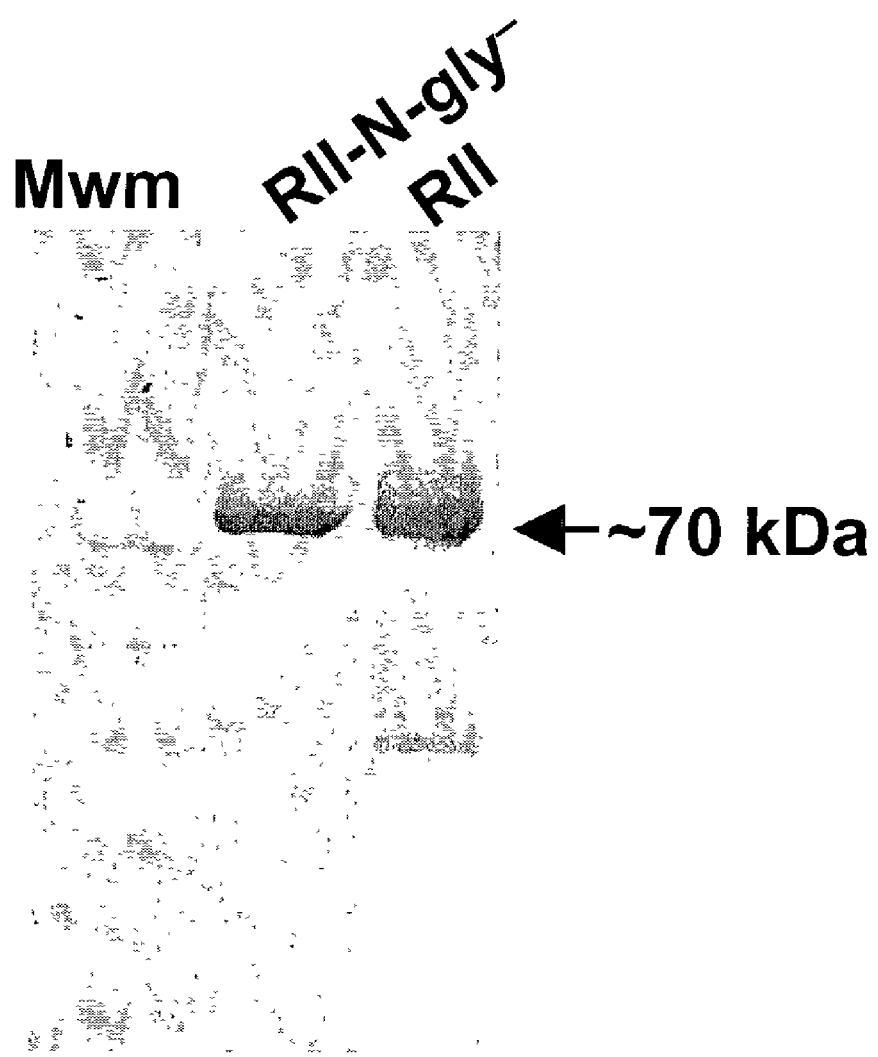
FIG. 11 is a photograph of Coomassie-stained SDS-PAGE gel of purified RII protein without (RII-N-Gly⁻) and with (RII) N-glycosylation.

To determine whether N-glycosylation alters the immunogenicity of RII, the properties of the glycosylated and non-glycosylated proteins were compared. The five putative N-glycosylation sites in the synthetic gene (SEQ ID NO:1 shown in FIG. 6) encoding EBA-175 RII protein (SEQ ID NO:2 shown in FIG. 7) were conservatively substituted to eliminate the possibility of N-glycosylation. The resulting synthetic gene sequence (SEQ ID NO:3 shown in FIG. 8) encodes the mutated RII protein (SEQ ID NO:4 shown in FIG. 9) lacking the putative N-glycosylation sites. The mutated gene was termed RII-N-Gly⁻ or RII-NG and cloned into the *P. pastoris* expression vector as schematically shown in FIG. 10. The synthetic gene with an in-frame stop codon and XhoI/XbaI linkers at the 5' and 3' ends, respectively was excised from the plasmid containing it with the restriction enzymes XhoI and XbaI. The −1.8 kb RII-N-Gly⁻ fragment was gel-purified with the Gel Extraction Kit (QIAGEN, Inc., Valencia, Calif.) and subcloned into the XhoI and XbaI sites in pPICZαA vector. The ligation mix was transformed into the Top 10 *Escherichia coli* dtrain (Invitrogen, San Diego, Calif.), and the transformants were screened by restriction enzyme analysis. The plasmid pPICZαA/RII-N-Gly⁻ containing the RII-N-Gly⁻ gene was selected and sequence verified. pPICZαA/RII-N-Gly⁻ plasmid DNA was prepared using Qiagen Plasmid Maxi Kit (Qiagen, Inc.), linearized with the restriction enzyme SacI (Life Technology, Gaithersburg, Md.), and transformed into *P. pastoris* host strain X33 (His4+Mut+, Invitrogen, San Diego, Calif.) by electroporation as suggested by the vendor. *P. pastoris* transformed with pPICZαA/RII-N-Gly⁻ was selected on YPD plates with 100, 200 or 500 μg/ml Zeocin. Sixteen transformants were selected and streaked for single colony separation on YPD+Zeocin at concentrations corresponding to the selection plates. Single colonies representing the 16 transformants were tested for expression of RII-NG in BMGY/BMMY media for 96 hours at 30° C., time-point samples were collected every 24 hours, and expression of RII-N-Gly⁻ was analyzed. Clones yielding higher levels of RII-N-Gly⁻ were selected for analysis of the complete time-course by Coomassie stain of SDS-PAGE gels and immunoblot with RII specific mAb R217 and rabbit polyclonal IgG. One was selected as the production clone. FIG. 11 shows the Coomassie-stained SDS-PAGE gel of the original (encoded by the nucleotide sequence SEQ ID NO:1) and mutant (encoded by the nucleotide sequence SEQ ID NO:2) purified RII protein with and without glycosylation.

EXAMPLE 10

Properties of the Mutated Non-N-glycosylated Recombinant RII Protein Expressed in *Pichia pastoris*

Figure 12:
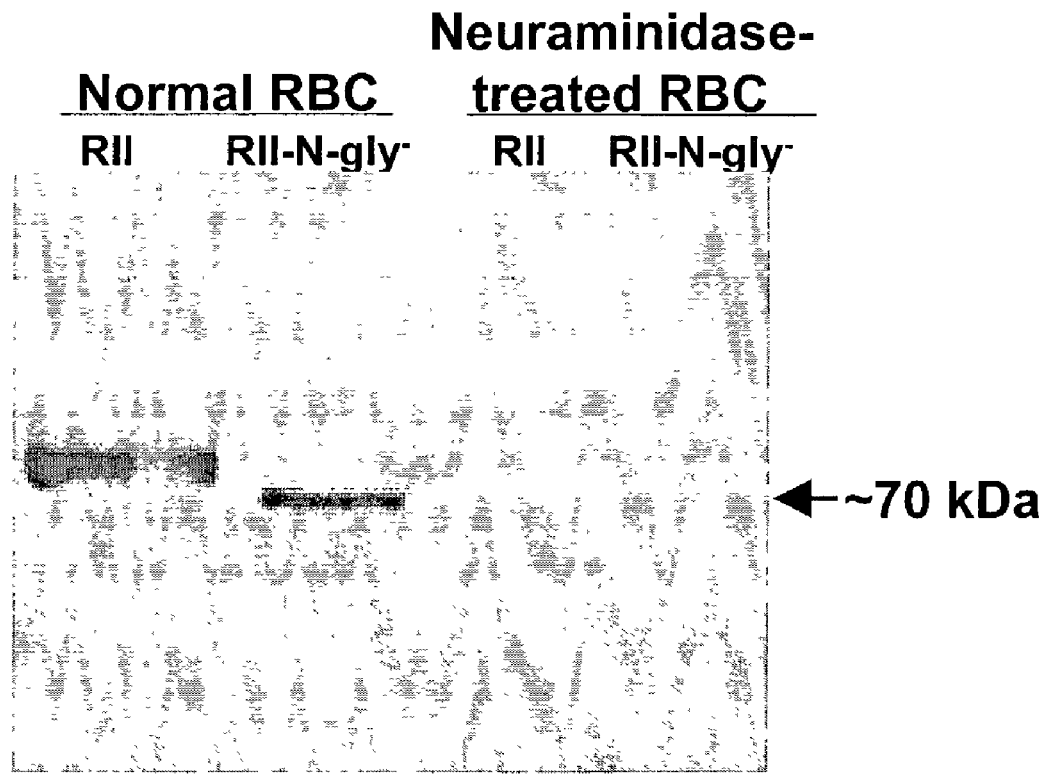
FIG. 12 is a photograph of an immunoblot showing the results of red blood cell (RBC) binding assay with human RBCs with or without neuraminidase treatment that removes sialic acid residues. Immunoblot shown in Panel B was probed with EBA-175 RII specific monoclonal antibody R216.
Figure 13:
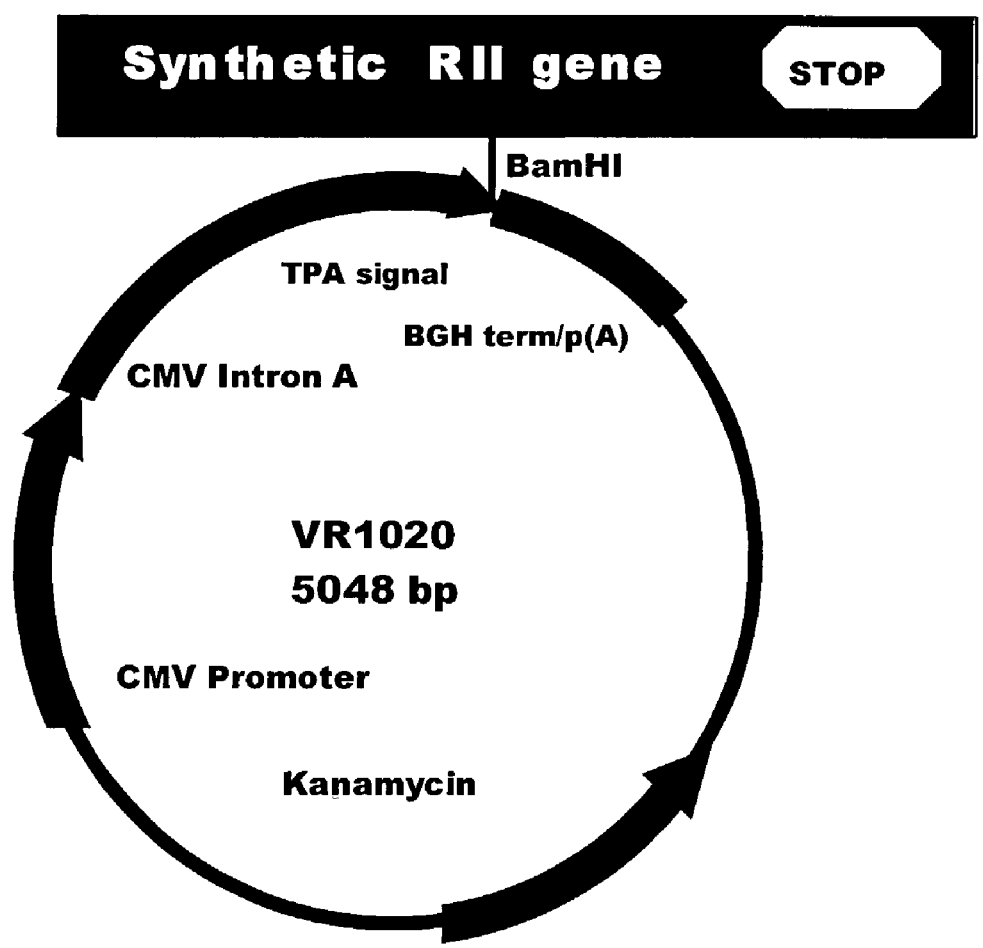
FIG. 13 is a scheme of the mammalian expression vector VR1020 (Vical Inc.) for the synthetic RII genes.
Figure 14:
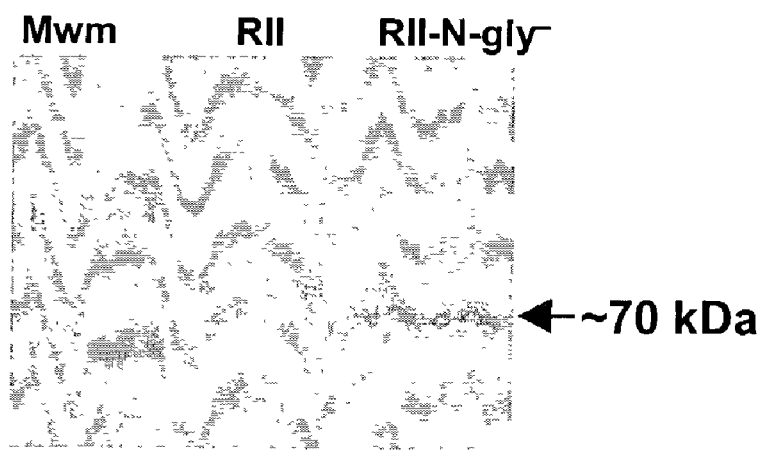
FIG. 14 is a photograph of an immunoblot (Western blot) showing that EBA-175 synthetic RII and RII-N-Gly⁻ DNA vaccines express similar levels of RII protein in vitro.
Figure 15:
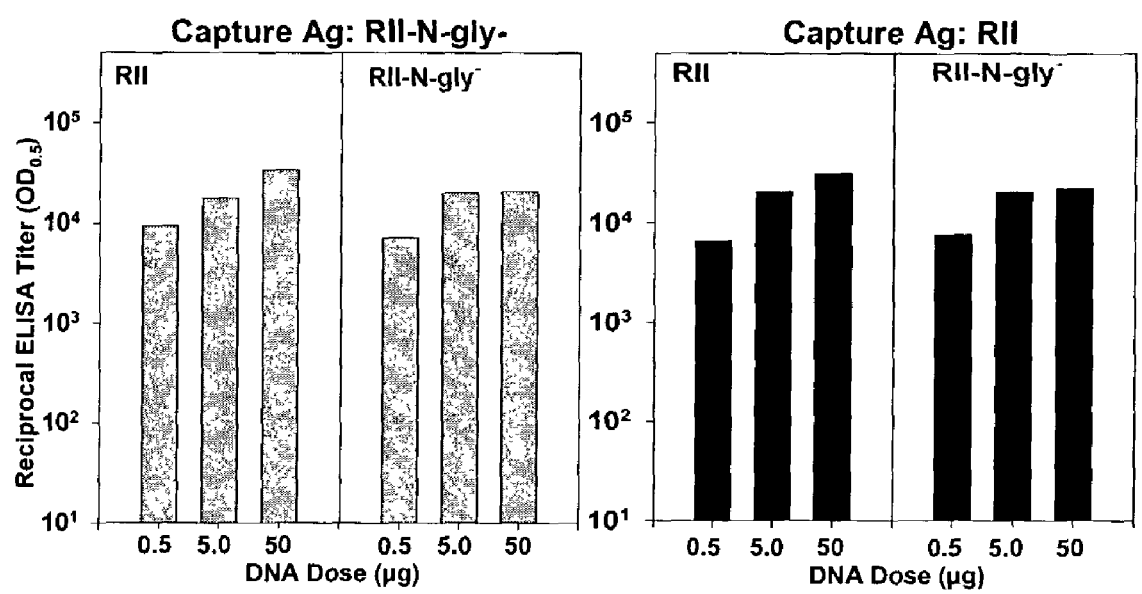
FIG. 15 is a bar graph showing specific antibody titers generated in vivo by EBA-175 synthetic RII and RII-N-Gly⁻ DNA vaccines.

The mutated RII protein showed a modification of N-glycosylation as determined by lectin blot. Non-N-glycosylated RII (RII-N-Gly⁻) purified by ion-exchange column chromatography showed identical binding characteristics as that of native EBA-175 in erythrocyte binding assays as shown in FIG. 12. Both native and mutated proteins bound erythrocytes in sialic-acid dependent manner. Further, non-N-glycosylated RII was recognized by conformationally dependent, neutralizing RII-specific monoclonal antibodies as determined by immunoblot.

EXAMPLE 11

The Effect of N-Glycosylation on the Immunogenicity of EBA-175 RII Protein Expressed in *Pichia pastoris*

Rabbits were immunized with *Pichia pastoris* derived N-glycosylated RII and non-N-glycosylated (RII-N-Gly⁻) proteins. The rabbits were immunized thrice with 100 μg recombinant protein in Freund's adjuvant or adjuvant alone for controls. Table 8 shows that rabbit antibodies against RII and RII-N-Gly⁻ blocked native EBA-175 erythrocyte binding and inhibited parasite growth of *P. falciparum* strains that invade erythrocytes in both a sialic acid dependent (FVO) and sialic acid independent (3D7) manner in vitro. As shown in Table 8, immune sera were also tested for recognition of parasites by inmmunofluorescence antibody assay, and blocking of EBA-175.

TABLE 8

Antibodies against recombinant RII and RII-N-Gly⁻ protein vaccines block function of EBA-175

| Rabbit No. | Recombinant P. pastoris RII vaccine[1] | Reciprocal IFA Titer | RII ELISA Titer[2] (RII capture asntigen) | RII ELISA Titer[2] (RII-N-Gly⁻ capture antigen) | Blocking Antibodies $IC_{50}$[3] | % growth inhibition of RBC invasion[4] FVO | 3D7 |
|---|---|---|---|---|---|---|---|
| 74 | RII | 160,000 | 937,296 | 623,374 | 9,305 | 22 | 25 |
| 75 | | 31 | 1,656,000 | 1,442,000 | 17,070 | 29 | |
| 76 | RII-N-Gly⁻ | 160,000 | 355,233 | 562,888 | 15,887 | 20 | 23 |
| 77 | | 160,000 | 244,534 | 407,154 | 12,721 | 18 | 17 |

[1]Rabbits 74/75, 76/77 and controls were immunized thrice with 100 mg recombinant protein in Freund's adjuvant or adjuvant alone for controls.
[2]Interpolated reciprocal RII ELISA titers are reported for an OD of 0.5 using either RII or RII-N-Gly⁻ for the capture antigen.
[3]Inhibitory concentration (IC) 50%: interpolated reciprocal serum concentration at which native [$^{35}$S] metabolically labeled EBA-175 RBC binding was blocked by 50%
[4]% Growth inhibition reported using purified rabbit IgG at 1.0 mg/mL compared to control. All values were statistically significant $p < 0.05$ According to the assay data presented in Table 8, N-linked glycosylation of EBA-175 by P. pastoris* does not alter the immunogenicity of RII.

EXAMPLE 12

The Effect of N-Glycosylation on the Immunogenicity of EBA-175 RII Protein Expressed in Mammalian Cells The mammalian expression vectors for the synthetic genes RII and RII-N-Gly$^-$ encoding N-glycosylated and non N-glycosylated EBA-175 RII protein were obtained by cloning each gene into the DNA vaccine plasmid VR 1020 (obtained from Vical, Inc.). The scheme of the cloning is shown in FIG. 13. Each synthetic genes was cloned in frame into the BamHI restriction site. EBA-175 N-glycosylated (RII) and non-N-glycosylated (RII-N-Gly$^-$ pr RII-NG) RII DNA vaccines showed similar levels of protein expression by transient transfection in vitro, as shown in FIG. 14. As seen in FIG. 14, RII-N-Gly$^-$ protein derived from mammalian cells transiently transfected with the RII-N-Gly$^-$ DNA vaccine also showed decrease in molecular mass by immunoblot indicating a modification of N-glycosylation.

Immunogenicity of mammalian-derived RII-N-Gly$^-$ and RII proteins was also tested. Groups of 10 outbred mice were immunized intradermally thrice at two-week intervals with 0.5, 5, and 50 μg of VR1020 synthetic RII or RII-N-Gly$^-$ DNA vaccines in phosphate buffered saline (PBS). Antibody responses were measured two weeks after the final immunization by enzyme-linked immunosorbent assay (ELISA) using *P. pastoris* derived RII-N-Gly$^-$ or RII protein as capture-antigen, as shown in FIG. 15. As seen in the bar graphs in FIG. 15, EBA-175 N-glycosylated (RII) and non-N-glycosylated (RII-N-Gly$^-$) RII DNA vaccines induced similar RII-specific antibody titers in outbred mice in vivo. Analysis of pooled anti-RII and anti-RII-N-Gly$^-$ specific mouse sera showed that the EBA-175 blocking titers were also similar.

EXAMPLE 13

Large-Scale Fermentation Process for Production of EBA-175 RII-N-Gly$^-$ (RII-NG)

The inoculum culture was prepared by inoculating one vial of frozen glycerol stock into 125 mL of BMGY media (0.4 mg/L Biotin; 10 g/L Glycerol; 13.4 g/L Yeast Nitrogen Base; 20 g/L Peptone; 10 g/L Yeast Extract; 0.1M Potassium Phosphate Buffer, pH 6.0) in a 500 ml flask and incubating the culture at 250 rpm and 30° C. for approximately 24 hours to a final $OD_{600nm.}$ of 15–25, followed by transferring 20 ml of the resulting culture into 250 ml BMG medium (0.4 mg/L Biotin; 10 g/L Glycerol; 13.4 g/L Yeast Nitrogen Base; 0.1M Potassium Phosphate Buffer, pH 6.0) in a 2 L Shake Flask and incubating it at 250 rpm and 30° C. for approximately 14 hours to a final $OD_{600nm}$ of 15–30. Table 9 shows the composition of fermentation medium, wherein Trace Salts Solution (Table 10) was added upon sterilization. The fermentation consisted of four main phases: batch glycerol, fed-batch glycerol, methanol ramp and methanol soak. The batch glycerol phase was the beginning phase which utilized the initial charge of glycerol as the carbon source. This phase lasted for approximately 24 hours. A sharp DO spike characterizes the end of this phase. The spike indicated the depletion of the carbon source. The fed-batch glycerol phase is initiated at a set flow (16.6 g/L/hr) immediately following the batch glycerol phase. The fed-batch glycerol phase lasted for 6 hours. During the final two hours of the fed-batch phase, the pH was ramped linearly from 5.0 to 6.0, and temperature was linearly decreased from 30 C. to 24° C. The methanol ramp phase was initiated immediately following the fed-batch glycerol phase. The methanol was used as a carbon source and as a product inducer. EBA-175 WING was produced as a secreted protein. During this phase, the methanol flow rate to the fermentor was ramped linearly from 1.5 to 8.5 mL/L/hr with a ramping rate of 1 ml/L/$hr^2$. The final phase of the fermentation was the methanol induction phase, conducted at 20° C., pH 6.0, with wet cell mass at induction of aproximately 200 g/L. Methanol continued to be used as a carbon source and product inducer. During this phase methanol was fed to the fermentor at a set rate of 8.5 mL/L/hr for 82 hours. The fermentation supernatant was collected by centrifugation and stored at −20° C. for further purifcation. Final EBA-175 RII-NG concentration was approximately 1.4–1.8 g/L fermentation supernatant. The final weight cell weight (WCW) is approximately 480 g/L.

TABLE 9

Pre-inoculum specifications of fermentation medium*

| Component | Concentration |
|---|---|
| Calcium Sulfate, dihydrate ($CaSO_4 \cdot 2H_2O$) | 0.93 g/L |
| Potassium Sulfate ($K_2SO_4$) | 18.2 g/L |
| Magnesium Sulfate ($MgSO4 \cdot 7H_2O$) | 14.9 g/L |
| Potassium Hydroxide (KOH) | 4.13 g/L |
| Phosphoric Acid ($H_3PO_4$) | 11.35 mL/L |
| Glycerol | 40 g/L |
| $PTM_4$ Trace Salts | 4.375 mL/L |
| Antifoaming agent KFO 880 (Kabo chemicals, Inc. Cheyenne, WY) | |

*Sterilize at 121° c. for no less than 20 minutes and no more than 30 minutes

TABLE 10

$PTM_4$ Solution*

| Component | Concentration |
|---|---|
| Cupric Sulfate ($CuSO4 \cdot 5H_2O$) | 2 g/L |
| Sodium Iodide (NaI) | 0.08 g/L |
| Manganese Sulfate ($MnSO4 \cdot H2O$) | 3 g/L |
| Sodium Molybdate ($Na_2MoO_4 \cdot 2H_2O$) | 0.2 g/L |
| Boric Acid ($H_3BO_3$) | 0.02 g/L |
| Cobalt Chloride ($CoCl_2 \cdot 6H_2O$) | 0.5 g/L |
| Zinc Chloride ($ZnCl_2$) | 7 g/L |
| Ferric Sulfate ($FeSO_4 \cdot 7H2O$) | 22 g/L |
| d-Biotin | 0.2 g/L |
| Sulfuric Acid ($H_2SO_4$) | 1 mL/L |

*Filter sterilized with 0.2 µm filter unit

EXAMPLE 14

Purification Process for Piciha-Derived Recombinant EBA-175 RII-N-Gly⁻ (RII-NG)

A process for purification of RII-N-Gly⁻ (RII-NG) was developed. The process consisted of one Tangential Flow Filtration (TFF) step and four chromatography steps. Cation-exchange chromatography (CEX) is used as a capture step, followed by a mixed mode hydrophobic charge induction chromatography (HCIC), then a polishing step consisting of anion- and cation-exchange chromatography (Q/CEX) in tandem, and finally a UF/DF step to adjust protein concentration and buffer strengths. The preferred protocol for the individual purification steps are as follows.

Biosepra® CM HyperD F (Ciphergen Biosystems Inc., Fremont, Calif.) Cation Exchange Chromatography (CEX)
Equilibration: 7 column volumes (CV) of 25 mM Phosphate (monobasic)/50 mM
Citrate, pH 5.6
Load sample: 4-fold dilution (1:3) with 66.7 mM Citrate, pH 5.6
Wash: 5 CV 50 mM Citrate+200 mM NaCl, pH 5.6
Elution: 7 CV 50 mM Citrate+450 mM NaCl, pH 5.6
Strip: 3 CV 2 M NaCl
CIP: 3 CV 1.0 M NaOH, (hold 1 hour)
Store: 5 CV 50 mM NaOH+1.0 M NaCl Biosepra® MEP HyperCel Hydrophobic Interaction Chromatography (HCIC)
Wash: 5 CV Water
Equilibrate: 7 CV 50 mM Citrate buffer+2.25 M NaCl, pH 6.0
Load sample diluted with 5 M NaCl, 70% volume, ~170 mS/cm
Wash: 5 CV 50 mM Citrate+1.75 M NaCl, pH 5.6
Elution: 7C V 20 mM Citric Acid buffer, pH 4.8
Strip: 3 CV 200 mM Citric Acid buffer, pH 3
Wash: 3 CV Water
CIP: 3 CV 1.0 M NaOH
Store: 3 CV 50 mM NaOH Mustang Q (Pall Corporation, East Hills, N.Y.) Anion-exchange Chromatography Both DNA and endotoxin were effectively removed using the Q membrane while maintaining a high flow rate across the membrane. Comparison of DNA removal at 10 CV/min versus 30 CV/min showed a slight reduction in the amount of DNA bound to the membrane (~10%). A preferred buffer for this step was 10 mM Tris/5 mM Citrate, pH 7.5. The step was run separately or in tandem with the following CEX step.

SPHP (Pharmacia, Peapack, N.J.) Cation-Exchange Chromatography

The method was run on the BioCad® 700E (Applied Biosystems, Foster City, Calif.) workstation as follows:
Flow Rate: 300 cm/hr (4.0 mL/min)
Charge: 5 CV 2 M NaCl
Equilibration: 6 CV 10 mM Tris/5 mM Citrate pH 7.5
Load sample: 17.5 mg/mL (100 mg/mL)
Wash 1 w/Q coin: 2 CV 10 mM Tris/5 mM Citrate pH 7.5
Wash 2 SpHP: 4 CV 25 mM Phosphate pH 7.5+210 mM NaCl
Elution: 5 CV 25 mM Phosphate pH 7.5+350 mM NaCl
CIP: 3 CV 2 M NaCl+1 N NaOH
Store: 3 CV 0.1 N NaOH A binding capacity of 17 mg/ml was achieved under these conditions.

The purified EBA-175 RII-N-Gly⁻ protein had a molecular mass of 72048 Daltons as determined by mass spectrometry. This was 1561 Daltons less than that of the theoretical value (73609 Daltons). According to N-terminal sequencing analysis, purified EBA 175 RII-N-Gly⁻ protein possessed the correct N-terminal glycine residue, and there was no evidence to suggest the presence of internal cleavage of the purified RII-N-Gly⁻ protein. The molecular weight discrepancy appeared to come from a C-terminal truncation. Based on the predicted sequence, a deletion of 14 amino acid residues ([603]DVPISIIRNNEQTS[616]; SEQ ID NO:5) from the expected C-terminus of EBA-175 RII-N-Gly⁻ could result in a truncated molecule with a molecular mass of 72041 Daltons, which is essentially the same as the predicted molecular mass of the protein having a C-terminal truncation. The C-terminal truncation was confirmed by Lys-C peptide mapping of purified EBA-175 RII-N-Gly⁻. Among five different lots tested so far, no evidence of the presence of this intact C-terminal fragment has been identified.

The above purification process was further developed by performing integration runs at a scale equivalent to 1/16th of the projected production scale (Table 11). The process was robust as shown by the measurements of in-process samples and final bulks. The overall recovery of the process was about 50%, excluding the harvest step. The purity of the final bulk was greater than 99% as determined by high pressure liquid chromatography (HPLC). Operational parameters, such as column bed height, flow rate, hold times and temperature should be maintained as closely as possible to that of the projected production.

TABLE 11

Parameters for integration runs

| Purification Train | Step | Configuration (inner diamter × height) | Bed Volume ml | Average Load (g) | Mean Capacity (g/L) | Linear Flow Rate cm/hr |
|---|---|---|---|---|---|---|
| Capture (CEX) | CM HyperD F | 5 cm × 11 cm | 215 | 4.1 | >19 | 400 |
| Polishing 1 (HCIC) | MEP-HyperCel | 5 cm × 13 cm | 255 | 2.9 | >12 | 200 |
| Polishing 2 (AEX/CEX tandem) | Q/SPHP | 10 ml/5 cm × 12 cm | 10/235 | 2.3 | N/A > 10 | 280 |
| Ultrafiltration/ Diafiltration | UF/DF | 0.2 ft$^2$ 5K PES | 0.2 ft$^2$ | 2.0 | N/A | Flux = 21 Lft$^{-2}$hr$^{-1}$ |

REFERENCES

Orlandi, P. A., Klotz, F. W. and Haynes, J. D. A malaria invasion receptor, the 175-kilodalton erythrocyte binding antigen of *Plasmodium falciparum* recognizes the terminal neu5Ac(α2–3)gal-sequences of glycophorin A. *J. Cell Biol.* 116: 901–909 (1992).

Camus, D. and T. J. Hadley. A *Plasmodium falciparum* antigen that binds to host erythrocytes and merozoites. *Science.* 230(4725):553–6 (1985).

Sim, B. K., P. A. Orlandi, et al. Primary structure of the 175K *Plasmodium falciparum* erythrocyte binding antigen and identification of a peptide which elicits antibodies that inhibit malaria merozoite invasion. *J Cell Biol* 111(5 pt 1):1877–84 (1990).

Gurunathan, S., Klinman, D. M. & Seder, R. A. DNA vaccines: immunology application, and optimization*. *Annu Rev Immunol* 18, 927–74 (2000).

Sedegah, M., Hedstrom, R., Hobart, P. & Hoffman, S. L. Protection against malaria by immunization with plasmid DNA encoding circumsporozoite protein. *Proc Natl Acad Sci USA* 91, 9866–70 (1994).

Doolan, D. L. et al. Circumventing genetic restriction of protection against malaria with multigene G\NA immunization: CD8+ cell-, interferon gamma-, and nitric oxide-dependent immunity. *J Exp Med* 183, 1739–46 (1996).

Becker, S. I. et al. Protection of mice against *Plasmodium yoelii* sporozoite challenge with *P. yoelii* merozoite surface protein 1 DNA vaccines. *Infect Immun* 66, 3457–61 (1988).

Wang, R. et al. Induction of antigen-specific cytotoxic T lymphocytes in humans by a malaria DNA vaccine. *Science* 282, 476–80 (1998)

Ikemura, T. Codon usage and tRNA content in unicellular and multicellular organisms. *Mol Biol Evol* 2, 13–34 (1985).

Sharp, P. M. & Li, W. H. The codon Adaptation Index—a measure of directional synonymous codon usage bias, and its potential applications. *Nucleic Acids Res* 15, 1281–95 (1987).

Sim, B. L. K. EBA-175: an erythrocyte-binding ligand of *Plasmodium falciparum. Parasitol. Today* 11, 213–217 (1995).

Sim, B. K. L., Chitnis, C. E., Wasniowska, K., Hadley, T. J., Miller, L. H. Receptor and ligand domains for invasion of erythrocytes of *Plasmodium falciparum. Science* 264, 1941–44 (1994).

Narum, D. L. et al. Antibodies against the *Plasmodium falciparum* receptor binding domain of EBA-175 block invasion pathways that do not involve sialic acids. *Infect Immun* 68, 1964,66 (2000).

Hoffman, S. L., Rogers, W. O., Carucci, D. J. & Venter, H. C. From genomics to vaccines: malaria as a model system [comment]. *Nat Med* 4, 1351–53 (1998).

Sambrook, J., Russel, D. W. and Sambrook, J. Molecular Cloning: A Laboratory Manual, Cold Spring Harbor Laboratory, 2001.

Sim, B. K. L., Narum, D. L., Liang, H., Fuhrmann, S. R., Obaldia III, N., Gramzinski, R., Aguiar, J., Haynes, J. D., Moch, K., and Hoffman, S. L. (2001) *Plasmodium falciparum* EBA-175 Region II DNA Vaccination Induces Biologically Active Antibodies. *Mol. Med.* 7: 247–254.

Jones, T. R., Narum, D. L., Gozalo, A. S., Aguiar, J., Fuhrmann, S., Liang, H., Haynes, J. D., Lucas, C., Luu, T., Magill, A., Hoffman, S. L., and Sim, B. K. L. (2001) Immunization of Aotus Monkeys with *Plasmodium falciparum* EBA-175 Region II DNA and Protein Vaccines: Effects of Boosting on Immunogenicity and Protection. *J. Infect. Dis.* 183: 303–312.

All references recited herein are hereby incorporated by references in their entireties.

SEQUENCE LISTING

```
<160> NUMBER OF SEQ ID NOS: 7

<210> SEQ ID NO 1
<211> LENGTH: 1848
<212> TYPE: DNA
<213> ORGANISM: Artificial Sequence
<220> FEATURE:
<223> OTHER INFORMATION: Synthetic EBA-175 RII
```

<220> FEATURE:
<221> NAME/KEY: CDS
<222> LOCATION: (1)..(1848)

<400> SEQUENCE: 1

```
ggc cgc aac acc tcc tcc aac aac gag gtg ctg tcc aac tgc cgc gag      48
Gly Arg Asn Thr Ser Ser Asn Asn Glu Val Leu Ser Asn Cys Arg Glu
1               5                   10                  15 aag cgc aag ggc atg aag tgg gac tgc aag aag aag aac gac cgc tcc      96
Lys Arg Lys Gly Met Lys Trp Asp Cys Lys Lys Lys Asn Asp Arg Ser
            20                  25                  30 aac tac gtg tgc atc ccc gac cgc cgc atc cag ctg tgc atc gtg aac     144
Asn Tyr Val Cys Ile Pro Asp Arg Arg Ile Gln Leu Cys Ile Val Asn
        35                  40                  45 ctg tcc atc atc aag acc tac acc aag gag acc atg aag gac cac ttc     192
Leu Ser Ile Ile Lys Thr Tyr Thr Lys Glu Thr Met Lys Asp His Phe
    50                  55                  60 atc gag gcc tcc aag aag gag tcc cag ctg ctg ctg aag aag aac gac     240
Ile Glu Ala Ser Lys Lys Glu Ser Gln Leu Leu Leu Lys Lys Asn Asp
65                  70                  75                  80 aac aag tac aac tcc aag ttc tgc aac gac ctg aag aac tcc ttc ctg     288
Asn Lys Tyr Asn Ser Lys Phe Cys Asn Asp Leu Lys Asn Ser Phe Leu
                85                  90                  95 gac tac ggc cac ctg gcc atg ggc aac gac atg gac ttc ggc ggc tac     336
Asp Tyr Gly His Leu Ala Met Gly Asn Asp Met Asp Phe Gly Gly Tyr
            100                 105                 110 tcc acc aag gcc gag aac aag atc cag gag gtg ttc aag ggc gcc cac     384
Ser Thr Lys Ala Glu Asn Lys Ile Gln Glu Val Phe Lys Gly Ala His
        115                 120                 125 ggc gag atc tcc gag cac aag atc aag aac ttc cgc aag aag tgg tgg     432
Gly Glu Ile Ser Glu His Lys Ile Lys Asn Phe Arg Lys Lys Trp Trp
    130                 135                 140 aac gag ttc cgc gag aag ctg tgg gag gcc atg ctg tcc gag cac aag     480
Asn Glu Phe Arg Glu Lys Leu Trp Glu Ala Met Leu Ser Glu His Lys
145                 150                 155                 160 aac aac atc aac aac tgc aag aac atc ccc cag gag gag ctg cag atc     528
Asn Asn Ile Asn Asn Cys Lys Asn Ile Pro Gln Glu Glu Leu Gln Ile
                165                 170                 175 acc cag tgg atc aag gag tgg cac ggc gag ttc ctg ctg gag cgc gac     576
Thr Gln Trp Ile Lys Glu Trp His Gly Glu Phe Leu Leu Glu Arg Asp
            180                 185                 190 aac cgc tcc aag ctg ccc aag tcc aag tgc aag aac aac acc ctg tac     624
Asn Arg Ser Lys Leu Pro Lys Ser Lys Cys Lys Asn Asn Thr Leu Tyr
        195                 200                 205 gag gcc tgc gag aag gag tgc atc gac ccc tgc atg aag tac cgc gac     672
Glu Ala Cys Glu Lys Glu Cys Ile Asp Pro Cys Met Lys Tyr Arg Asp
    210                 215                 220 tgg atc atc cgc tcc aag ttc gag tgg cac acc ctg tcc aag gag tac     720
Trp Ile Ile Arg Ser Lys Phe Glu Trp His Thr Leu Ser Lys Glu Tyr
225                 230                 235                 240 gag acc cag aag gtg ccc aag gag aac gcc gag aac tac ctg atc aag     768
Glu Thr Gln Lys Val Pro Lys Glu Asn Ala Glu Asn Tyr Leu Ile Lys
                245                 250                 255 atc tcc gag aac aag aac gac gcc aag gtg tcc ctg ctg ctg aac aac     816
Ile Ser Glu Asn Lys Asn Asp Ala Lys Val Ser Leu Leu Leu Asn Asn
            260                 265                 270 tgc gac gcc gag tac tcc aag tac tgc gac tgc aag cac acc acc acc     864
Cys Asp Ala Glu Tyr Ser Lys Tyr Cys Asp Cys Lys His Thr Thr Thr
        275                 280                 285
```

| | |
|---|---|
| ctg gtg aag tcc gtg ctg aac ggc aac gac aac acc atc aag gag aag<br>Leu Val Lys Ser Val Leu Asn Gly Asn Asp Asn Thr Ile Lys Glu Lys<br>290                       295                          300 | 912 |
| cgc gag cac atc gac ctg gac gac ttc tcc aag ttc ggc tgc gac aag<br>Arg Glu His Ile Asp Leu Asp Asp Phe Ser Lys Phe Gly Cys Asp Lys<br>305                       310                          315                  320 | 960 |
| aac tcc gtg gac acc aac acc aag gtg tgg gag tgc aag aag ccc tac<br>Asn Ser Val Asp Thr Asn Thr Lys Val Trp Glu Cys Lys Lys Pro Tyr<br>                       325                          330                       335 | 1008 |
| aag ctg tcc acc aag gac gtg tgc gtg ccc ccc cgc cgc cag gag ctg<br>Lys Leu Ser Thr Lys Asp Val Cys Val Pro Pro Arg Arg Gln Glu Leu<br>                       340                          345                    350 | 1056 |
| tgc ctg ggc aac atc gac cgc atc tac gac aag aac ctg ctg atg atc<br>Cys Leu Gly Asn Ile Asp Arg Ile Tyr Asp Lys Asn Leu Leu Met Ile<br>               355                          360                       365 | 1104 |
| aag gag cac atc ctg gcc atc gcc atc tac gag tcc cgc atc ctg aag<br>Lys Glu His Ile Leu Ala Ile Ala Ile Tyr Glu Ser Arg Ile Leu Lys<br>370                       375                          380 | 1152 |
| cgc aag tac aag aac aag gac gac aag gag gtg tgc aag atc atc aac<br>Arg Lys Tyr Lys Asn Lys Asp Asp Lys Glu Val Cys Lys Ile Ile Asn<br>385                       390                          395                  400 | 1200 |
| aag acc ttc gcc gac atc cgc gac atc atc ggc ggc acc gac tac tgg<br>Lys Thr Phe Ala Asp Ile Arg Asp Ile Ile Gly Gly Thr Asp Tyr Trp<br>                       405                          410                       415 | 1248 |
| aac gac ctg tcc aac cgc aag ctg gtg ggc aag atc aac acc aac tcc<br>Asn Asp Leu Ser Asn Arg Lys Leu Val Gly Lys Ile Asn Thr Asn Ser<br>                       420                          425                    430 | 1296 |
| aac tac gtg cac cgc aac aag cag aac gac aag ctg ttc cgc gac gag<br>Asn Tyr Val His Arg Asn Lys Gln Asn Asp Lys Leu Phe Arg Asp Glu<br>               435                          440                       445 | 1344 |
| tgg tgg aag gtg atc aag aag gac gtg tgg aac gtg atc tcc tgg gtg<br>Trp Trp Lys Val Ile Lys Lys Asp Val Trp Asn Val Ile Ser Trp Val<br>450                       455                          460 | 1392 |
| ttc aag gac aag acc gtg tgc aag gag gac gac atc gag aac atc ccc<br>Phe Lys Asp Lys Thr Val Cys Lys Glu Asp Asp Ile Glu Asn Ile Pro<br>465                       470                          475                  480 | 1440 |
| cag ttc ttc cgc tgg ttc tcc gag tgg ggc gac gac tac tgc cag gac<br>Gln Phe Phe Arg Trp Phe Ser Glu Trp Gly Asp Asp Tyr Cys Gln Asp<br>                       485                          490                    495 | 1488 |
| aag acc aag atg atc gag acc ctg aag gtg gag tgc aag gag aag ccc<br>Lys Thr Lys Met Ile Glu Thr Leu Lys Val Glu Cys Lys Glu Lys Pro<br>               500                          505                   510 | 1536 |
| tgc gag gac gac aac tgc aag cgc aag tgc aac tcc tac aag gag tgg<br>Cys Glu Asp Asp Asn Cys Lys Arg Lys Cys Asn Ser Tyr Lys Glu Trp<br>515                       520                          525 | 1584 |
| atc tcc aag aag aag gag gag tac aac aag cag gcc aag cag tac cag<br>Ile Ser Lys Lys Lys Glu Glu Tyr Asn Lys Gln Ala Lys Gln Tyr Gln<br>               530                          535                    540 | 1632 |
| gag tac cag aag ggc aac aac tac aag atg tac tcc gag ttc aag tcc<br>Glu Tyr Gln Lys Gly Asn Asn Tyr Lys Met Tyr Ser Glu Phe Lys Ser<br>545                       550                          555                  560 | 1680 |
| atc aag ccc gag gtg tac ctg aag aag tac tcc gag aag tgc tcc aac<br>Ile Lys Pro Glu Val Tyr Leu Lys Lys Tyr Ser Glu Lys Cys Ser Asn<br>                       565                          570                    575 | 1728 |
| ctg aac ttc gag gac gag ttc aag gag gag ctg cac tcc gac tac aag<br>Leu Asn Phe Glu Asp Glu Phe Lys Glu Glu Leu His Ser Asp Tyr Lys<br>               580                          585                    590 | 1776 |

```
aac aag tgc acc atg tgc ccc gag gtg aag gac gtg ccc atc tcc atc      1824
Asn Lys Cys Thr Met Cys Pro Glu Val Lys Asp Val Pro Ile Ser Ile
        595                 600                 605 atc cgc aac aac gag cag acc tcc                                      1848
Ile Arg Asn Asn Glu Gln Thr Ser
    610             615
```

<210> SEQ ID NO 2
<211> LENGTH: 616
<212> TYPE: PRT
<213> ORGANISM: Artificial Sequence
<220> FEATURE:
<223> OTHER INFORMATION: Synthetic EBA-175 RII

<400> SEQUENCE: 2

```
Gly Arg Asn Thr Ser Asn Asn Glu Val Leu Ser Asn Cys Arg Glu
1               5                   10                  15

Lys Arg Lys Gly Met Lys Trp Asp Cys Lys Lys Asn Asp Arg Ser
                20                  25                  30

Asn Tyr Val Cys Ile Pro Asp Arg Arg Ile Gln Leu Cys Ile Val Asn
            35                  40                  45

Leu Ser Ile Ile Lys Thr Tyr Thr Lys Glu Thr Met Lys Asp His Phe
50                  55                  60

Ile Glu Ala Ser Lys Lys Glu Ser Gln Leu Leu Leu Lys Lys Asn Asp
65                  70                  75                  80

Asn Lys Tyr Asn Ser Lys Phe Cys Asn Asp Leu Lys Asn Ser Phe Leu
                85                  90                  95

Asp Tyr Gly His Leu Ala Met Gly Asn Asp Met Asp Phe Gly Gly Tyr
                100                 105                 110

Ser Thr Lys Ala Glu Asn Lys Ile Gln Glu Val Phe Lys Gly Ala His
            115                 120                 125

Gly Glu Ile Ser Glu His Lys Ile Lys Asn Phe Arg Lys Lys Trp Trp
130                 135                 140

Asn Glu Phe Arg Glu Lys Leu Trp Glu Ala Met Leu Ser Glu His Lys
145                 150                 155                 160

Asn Asn Ile Asn Asn Cys Lys Asn Ile Pro Gln Glu Glu Leu Gln Ile
                165                 170                 175

Thr Gln Trp Ile Lys Glu Trp His Gly Glu Phe Leu Leu Glu Arg Asp
            180                 185                 190

Asn Arg Ser Lys Leu Pro Lys Ser Lys Cys Lys Asn Asn Thr Leu Tyr
        195                 200                 205

Glu Ala Cys Glu Lys Glu Cys Ile Asp Pro Cys Met Lys Tyr Arg Asp
210                 215                 220

Trp Ile Ile Arg Ser Lys Phe Glu Trp His Thr Leu Ser Lys Glu Tyr
225                 230                 235                 240

Glu Thr Gln Lys Val Pro Lys Glu Asn Ala Glu Asn Tyr Leu Ile Lys
                245                 250                 255

Ile Ser Glu Asn Lys Asn Asp Ala Lys Val Ser Leu Leu Asn Asn
                260                 265                 270

Cys Asp Ala Glu Tyr Ser Lys Tyr Cys Asp Cys Lys His Thr Thr Thr
            275                 280                 285

Leu Val Lys Ser Val Leu Asn Gly Asn Asp Asn Thr Ile Lys Glu Lys
        290                 295                 300

Arg Glu His Ile Asp Leu Asp Asp Phe Ser Lys Phe Gly Cys Asp Lys
305                 310                 315                 320
```

```
Asn Ser Val Asp Thr Asn Thr Lys Val Trp Glu Cys Lys Lys Pro Tyr
                325                 330                 335

Lys Leu Ser Thr Lys Asp Val Cys Val Pro Arg Arg Gln Glu Leu
            340                 345                 350

Cys Leu Gly Asn Ile Asp Arg Ile Tyr Asp Lys Asn Leu Leu Met Ile
            355                 360                 365

Lys Glu His Ile Leu Ala Ile Ala Ile Tyr Glu Ser Arg Ile Leu Lys
        370                 375                 380

Arg Lys Tyr Lys Asn Lys Asp Lys Glu Val Cys Lys Ile Ile Asn
385                 390                 395                 400

Lys Thr Phe Ala Asp Ile Arg Asp Ile Gly Gly Thr Asp Tyr Trp
                405                 410                 415

Asn Asp Leu Ser Asn Arg Lys Leu Val Gly Lys Ile Asn Thr Asn Ser
            420                 425                 430

Asn Tyr Val His Arg Asn Lys Gln Asn Asp Lys Leu Phe Arg Asp Glu
        435                 440                 445

Trp Trp Lys Val Ile Lys Lys Asp Val Trp Asn Val Ile Ser Trp Val
    450                 455                 460

Phe Lys Asp Lys Thr Val Cys Lys Glu Asp Asp Ile Glu Asn Ile Pro
465                 470                 475                 480

Gln Phe Phe Arg Trp Phe Ser Glu Trp Gly Asp Asp Tyr Cys Gln Asp
                485                 490                 495

Lys Thr Lys Met Ile Glu Thr Leu Lys Val Glu Cys Lys Glu Lys Pro
            500                 505                 510

Cys Glu Asp Asp Asn Cys Lys Arg Lys Cys Asn Ser Tyr Lys Glu Trp
        515                 520                 525

Ile Ser Lys Lys Glu Glu Tyr Asn Lys Gln Ala Lys Gln Tyr Gln
    530                 535                 540

Glu Tyr Gln Lys Gly Asn Asn Tyr Lys Met Tyr Ser Glu Phe Lys Ser
545                 550                 555                 560

Ile Lys Pro Glu Val Tyr Leu Lys Lys Tyr Ser Glu Lys Cys Ser Asn
                565                 570                 575

Leu Asn Phe Glu Asp Glu Phe Lys Glu Glu Leu His Ser Asp Tyr Lys
            580                 585                 590

Asn Lys Cys Thr Met Cys Pro Glu Val Lys Asp Val Pro Ile Ser Ile
        595                 600                 605

Ile Arg Asn Asn Glu Gln Thr Ser
    610                 615

<210> SEQ ID NO 3
<211> LENGTH: 1848
<212> TYPE: DNA
<213> ORGANISM: Artificial Sequence
<220> FEATURE:
<223> OTHER INFORMATION: Synthetic EBA-175 RII
<220> FEATURE:
<221> NAME/KEY: CDS
<222> LOCATION: (1)..(1848)

<400> SEQUENCE: 3 ggc c

```
aac tac gtg tgc atc ccc gac cgc cgc atc cag ctg tgc atc gtg aac      144
Asn Tyr Val Cys Ile Pro Asp Arg Arg Ile Gln Leu Cys Ile Val Asn
         35                  40                  45 ctg gcc atc atc aag acc tac acc aag gag acc atg aag gac cac ttc      192
Leu Ala Ile Ile Lys Thr Tyr Thr Lys Glu Thr Met Lys Asp His Phe
 50                  55                  60 atc gag gcc tcc aag aag gag tcc cag ctg ctg ctg aag aag aac gac      240
Ile Glu Ala Ser Lys Lys Glu Ser Gln Leu Leu Leu Lys Lys Asn Asp
65                  70                  75                  80 aac aag tac aac tcc aag ttc tgc aac gac ctg aag aac tcc ttc ctg      288
Asn Lys Tyr Asn Ser Lys Phe Cys Asn Asp Leu Lys Asn Ser Phe Leu
             85                  90                  95 gac tac ggc cac ctg gcc atg ggc aac gac atg gac ttc ggc ggc tac      336
Asp Tyr Gly His Leu Ala Met Gly Asn Asp Met Asp Phe Gly Gly Tyr
                100                 105                 110 tcc acc aag gcc gag aac aag atc cag gag gtg ttc aag ggc gcc cac      384
Ser Thr Lys Ala Glu Asn Lys Ile Gln Glu Val Phe Lys Gly Ala His
             115                 120                 125 ggc gag atc tcc gag cac aag atc aag aac ttc cgc aag aag tgg tgg      432
Gly Glu Ile Ser Glu His Lys Ile Lys Asn Phe Arg Lys Lys Trp Trp
130                 135                 140 aac gag ttc cgc gag aag ctg tgg gag gcc atg ctg tcc gag cac aag      480
Asn Glu Phe Arg Glu Lys Leu Trp Glu Ala Met Leu Ser Glu His Lys
145                 150                 155                 160 aac aac atc aac aac tgc aag aac atc ccc cag gag gag ctg cag atc      528
Asn Asn Ile Asn Asn Cys Lys Asn Ile Pro Gln Glu Glu Leu Gln Ile
                165                 170                 175 acc cag tgg atc aag gag tgg cac ggc gag ttc ctg ctg gag cgc gac      576
Thr Gln Trp Ile Lys Glu Trp His Gly Glu Phe Leu Leu Glu Arg Asp
             180                 185                 190 aac cgc gcc aag ctg ccc aag tcc aag tgc aag aac aac gcc ctg tac      624
Asn Arg Ala Lys Leu Pro Lys Ser Lys Cys Lys Asn Asn Ala Leu Tyr
             195                 200                 205 gag gcc tgc gag aag gag tgc atc gac ccc tgc atg aag tac cgc gac      672
Glu Ala Cys Glu Lys Glu Cys Ile Asp Pro Cys Met Lys Tyr Arg Asp
210                 215                 220 tgg atc atc cgc tcc aag ttc gag tgg cac acc ctg tcc aag gag tac      720
Trp Ile Ile Arg Ser Lys Phe Glu Trp His Thr Leu Ser Lys Glu Tyr
225                 230                 235                 240 gag acc cag aag gtg ccc aag gag aac gcc gag aac tac ctg atc aag      768
Glu Thr Gln Lys Val Pro Lys Glu Asn Ala Glu Asn Tyr Leu Ile Lys
                245                 250                 255 atc tcc gag aac aag aac gac gcc aag gtg tcc ctg ctg ctg aac aac      816
Ile Ser Glu Asn Lys Asn Asp Ala Lys Val Ser Leu Leu Leu Asn Asn
             260                 265                 270 tgc gac gcc gag tac tcc aag tac tgc gac tgc aag cac acc acc acc      864
Cys Asp Ala Glu Tyr Ser Lys Tyr Cys Asp Cys Lys His Thr Thr Thr
             275                 280                 285 ctg gtg aag tcc gtg ctg aac ggc aac gac aac acc atc aag gag aag      912
Leu Val Lys Ser Val Leu Asn Gly Asn Asp Asn Thr Ile Lys Glu Lys
        290                 295                 300 cgc gag cac atc gac ctg gac gac ttc tcc aag ttc ggc tgc gac aag      960
Arg Glu His Ile Asp Leu Asp Asp Phe Ser Lys Phe Gly Cys Asp Lys
305                 310                 315                 320 aac tcc gtg gac acc aac acc aag gtg tgg gag tgc aag aag ccc tac     1008
Asn Ser Val Asp Thr Asn Thr Lys Val Trp Glu Cys Lys Lys Pro Tyr
                325                 330                 335 aag ctg tcc acc aag gac gtg tgc gtg ccc ccc cgc cgc cag gag ctg     1056
Lys Leu Ser Thr Lys Asp Val Cys Val Pro Pro Arg Arg Gln Glu Leu
             340                 345                 350
```

```
tgc ctg ggc aac atc gac cgc atc tac gac aag aac ctg ctg atg atc      1104
Cys Leu Gly Asn Ile Asp Arg Ile Tyr Asp Lys Asn Leu Leu Met Ile
        355                 360                 365 aag gag cac atc ctg gcc atc gcc atc tac gag tcc cgc atc ctg aag      1152
Lys Glu His Ile Leu Ala Ile Ala Ile Tyr Glu Ser Arg Ile Leu Lys
    370                 375                 380 cgc aag tac aag aac aag gac gac aag gag gtg tgc aag atc atc cag      1200
Arg Lys Tyr Lys Asn Lys Asp Asp Lys Glu Val Cys Lys Ile Ile Gln
385                 390                 395                 400 aag acc ttc gcc gac atc cgc gac atc atc ggc ggc acc gac tac tgg      1248
Lys Thr Phe Ala Asp Ile Arg Asp Ile Ile Gly Gly Thr Asp Tyr Trp
                405                 410                 415 aac gac ctg tcc aac cgc aag ctg gtg ggc aag atc aac acc aac tcc      1296
Asn Asp Leu Ser Asn Arg Lys Leu Val Gly Lys Ile Asn Thr Asn Ser
            420                 425                 430 aac tac gtg cac cgc aac aag cag aac gac aag ctg ttc cgc gac gag      1344
Asn Tyr Val His Arg Asn Lys Gln Asn Asp Lys Leu Phe Arg Asp Glu
        435                 440                 445 tgg tgg aag gtg atc aag aag gac gtg tgg aac gtg atc tcc tgg gtg      1392
Trp Trp Lys Val Ile Lys Lys Asp Val Trp Asn Val Ile Ser Trp Val
450                 455                 460 ttc aag gac aag acc gtg tgc aag gag gac gac atc gag aac atc ccc      1440
Phe Lys Asp Lys Thr Val Cys Lys Glu Asp Asp Ile Glu Asn Ile Pro
465                 470                 475                 480 cag ttc ttc cgc tgg ttc tcc gag tgg ggc gac gac tac tgc cag gac      1488
Gln Phe Phe Arg Trp Phe Ser Glu Trp Gly Asp Asp Tyr Cys Gln Asp
                485                 490                 495 aag acc aag atg atc gag acc ctg aag gtg gag tgc aag gag aag ccc      1536
Lys Thr Lys Met Ile Glu Thr Leu Lys Val Glu Cys Lys Glu Lys Pro
            500                 505                 510 tgc gag gac gac aac tgc aag cgc aag tgc aac tcc tac aag gag tgg      1584
Cys Glu Asp Asp Asn Cys Lys Arg Lys Cys Asn Ser Tyr Lys Glu Trp
        515                 520                 525 atc tcc aag aag aag gag gag tac aac aag cag gcc aag cag tac cag      1632
Ile Ser Lys Lys Lys Glu Glu Tyr Asn Lys Gln Ala Lys Gln Tyr Gln
    530                 535                 540 gag tac cag aag ggc aac aac tac aag atg tac tcc gag ttc aag tcc      1680
Glu Tyr Gln Lys Gly Asn Asn Tyr Lys Met Tyr Ser Glu Phe Lys Ser
545                 550                 555                 560 atc aag ccc gag gtg tac ctg aag aag tac tcc gag aag tgc tcc aac      1728
Ile Lys Pro Glu Val Tyr Leu Lys Lys Tyr Ser Glu Lys Cys Ser Asn
                565                 570                 575 ctg aac ttc gag gac gag ttc aag gag gag ctg cac tcc gac tac aag      1776
Leu Asn Phe Glu Asp Glu Phe Lys Glu Glu Leu His Ser Asp Tyr Lys
            580                 585                 590 aac aag tgc acc atg tgc ccc gag gtg aag gac gtg ccc atc tcc atc      1824
Asn Lys Cys Thr Met Cys Pro Glu Val Lys Asp Val Pro Ile Ser Ile
        595                 600                 605 atc cgc aac aac gag cag acc tcc                                       1848
Ile Arg Asn Asn Glu Gln Thr Ser
    610                 615

<210> SEQ ID NO 4
<211> LENGTH: 616
<212> TYPE: PRT
<213> ORGANISM: Artificial Sequence
<220> FEATURE:
<223> OTHER INFORMATION: Synthetic EBA-175 RII
```

<400> SEQUENCE: 4

```
Gly Arg Gln Thr Ser Ser Asn Asn Glu Val Leu Ser Asn Cys Arg Glu
 1               5                  10                  15

Lys Arg Lys Gly Met Lys Trp Asp Cys Lys Lys Asn Asp Arg Ser
             20                  25                  30

Asn Tyr Val Cys Ile Pro Asp Arg Arg Ile Gln Leu Cys Ile Val Asn
                 35                  40                  45

Leu Ala Ile Ile Lys Thr Tyr Thr Lys Glu Thr Met Lys Asp His Phe
 50                  55                  60

Ile Glu Ala Ser Lys Lys Glu Ser Gln Leu Leu Leu Lys Lys Asn Asp
 65                  70                  75                  80

Asn Lys Tyr Asn Ser Lys Phe Cys Asn Asp Leu Lys Asn Ser Phe Leu
                 85                  90                  95

Asp Tyr Gly His Leu Ala Met Gly Asn Asp Met Asp Phe Gly Gly Tyr
                100                 105                 110

Ser Thr Lys Ala Glu Asn Lys Ile Gln Glu Val Phe Lys Gly Ala His
             115                 120                 125

Gly Glu Ile Ser Glu His Lys Ile Lys Asn Phe Arg Lys Lys Trp Trp
130                 135                 140

Asn Glu Phe Arg Glu Lys Leu Trp Glu Ala Met Leu Ser Glu His Lys
145                 150                 155                 160

Asn Asn Ile Asn Asn Cys Lys Asn Ile Pro Gln Glu Glu Leu Gln Ile
                165                 170                 175

Thr Gln Trp Ile Lys Glu Trp His Gly Glu Phe Leu Leu Glu Arg Asp
            180                 185                 190

Asn Arg Ala Lys Leu Pro Lys Ser Lys Cys Lys Asn Asn Ala Leu Tyr
            195                 200                 205

Glu Ala Cys Glu Lys Glu Cys Ile Asp Pro Cys Met Lys Tyr Arg Asp
210                 215                 220

Trp Ile Ile Arg Ser Lys Phe Glu Trp His Thr Leu Ser Lys Glu Tyr
225                 230                 235                 240

Glu Thr Gln Lys Val Pro Lys Glu Asn Ala Glu Asn Tyr Leu Ile Lys
                245                 250                 255

Ile Ser Glu Asn Lys Asn Asp Ala Lys Val Ser Leu Leu Asn Asn
            260                 265                 270

Cys Asp Ala Glu Tyr Ser Lys Tyr Cys Asp Cys Lys His Thr Thr Thr
            275                 280                 285

Leu Val Lys Ser Val Leu Asn Gly Asn Asp Asn Thr Ile Lys Glu Lys
290                 295                 300

Arg Glu His Ile Asp Leu Asp Asp Phe Ser Lys Phe Gly Cys Asp Lys
305                 310                 315                 320

Asn Ser Val Asp Thr Asn Thr Lys Val Trp Glu Cys Lys Lys Pro Tyr
                325                 330                 335

Lys Leu Ser Thr Lys Asp Val Cys Val Pro Pro Arg Arg Gln Glu Leu
            340                 345                 350

Cys Leu Gly Asn Ile Asp Arg Ile Tyr Asp Lys Asn Leu Leu Met Ile
            355                 360                 365

Lys Glu His Ile Leu Ala Ile Ala Ile Tyr Glu Ser Arg Ile Leu Lys
370                 375                 380

Arg Lys Tyr Lys Asn Lys Asp Asp Lys Glu Val Cys Lys Ile Ile Gln
385                 390                 395                 400
```

-continued

Lys Thr Phe Ala Asp Ile Arg Asp Ile Ile Gly Gly Thr Asp Tyr Trp
            405                 410                 415

Asn Asp Leu Ser Asn Arg Lys Leu Val Gly Lys Ile Asn Thr Asn Ser
        420                 425                 430

Asn Tyr Val His Arg Asn Lys Gln Asn Asp Lys Leu Phe Arg Asp Glu
            435                 440                 445

Trp Trp Lys Val Ile Lys Lys Asp Val Trp Asn Val Ile Ser Trp Val
        450                 455                 460

Phe Lys Asp Lys Thr Val Cys Lys Glu Asp Ile Glu Asn Ile Pro
465                 470                 475                 480

Gln Phe Phe Arg Trp Phe Ser Glu Trp Gly Asp Tyr Cys Gln Asp
                485                 490                 495

Lys Thr Lys Met Ile Glu Thr Leu Lys Val Glu Cys Lys Glu Lys Pro
            500                 505                 510

Cys Glu Asp Asp Asn Cys Lys Arg Lys Cys Asn Ser Tyr Lys Glu Trp
            515                 520                 525

Ile Ser Lys Lys Lys Glu Glu Tyr Asn Lys Gln Ala Lys Gln Tyr Gln
        530                 535                 540

Glu Tyr Gln Lys Gly Asn Asn Tyr Lys Met Tyr Ser Glu Phe Lys Ser
545                 550                 555                 560

Ile Lys Pro Glu Val Tyr Leu Lys Lys Tyr Ser Glu Lys Cys Ser Asn
                565                 570                 575

Leu Asn Phe Glu Asp Glu Phe Lys Glu Glu Leu His Ser Asp Tyr Lys
            580                 585                 590

Asn Lys Cys Thr Met Cys Pro Glu Val Lys Asp Val Pro Ile Ser Ile
        595                 600                 605

Ile Arg Asn Asn Glu Gln Thr Ser
    610                 615

<210> SEQ ID NO 5
<211> LENGTH: 14
<212> TYPE: PRT
<213> ORGANISM: Plasmodium falciparum

<400> SEQUENCE: 5

Asp Val Pro Ile Ser Ile Ile Arg Asn Asn Glu Gln Thr Ser
1               5                   10

<210> SEQ ID NO 6
<211> LENGTH: 27
<212> TYPE: DNA
<213> ORGANISM: Artificial Sequence
<220> FEATURE:
<223> OTHER INFORMATION: Synthetic primer

<400> SEQUENCE: 6
atcgggatcc ggcccaacac ctcctcc                                    27

<210> SEQ ID NO 7
<211> LENGTH: 30
<212> TYPE: DNA
<213> ORGANISM: Artificial Sequence
<220> FEATURE:
<223> OTHER INFORMATION: Synthetic primer

<400> SEQUENCE: 7
atcgggatcc tcaggaggtc tctcgttgtt                                 30

We claim:

1. An isolated synthetic nucleotide sequence encoding a domain of the erythrocyte-binding protein of a malaria pathogen that infects humans, wherein codon usage of the synthetic nucleotide sequence is altered compared to a naturally occurring sequence of the erythrocyte-binding protein in order to approximate codon usage of a host of the malaria pathogen, wherein the host is a human, and wherein the domain of the erythrocyte-binding protein is the region II of in 3D7 (NIH) *Plasmodium falciparum* EBA-175 protein.

2. The synthetic nucleotide sequence of claim 1, wherein the codon-altered sequence is SEQ ID NO: 1.

3. The synthetic nucleotide sequence of claim 1, wherein the codon-altered sequence encodes the amino acid sequence SEQ ID NO: 2.

* * * * *

UNITED STATES PATENT AND TRADEMARK OFFICE
CERTIFICATE OF CORRECTION

PATENT NO. : 7,078,507 B2 Page 1 of 1
APPLICATION NO. : 10/293913
DATED : July 18, 2006
INVENTOR(S) : Narum et al.

It is certified that error appears in the above-identified patent and that said Letters Patent is hereby corrected as shown below:

In Col. 40, Line 1, Claim 1, after "of" delete "in" and insert -- strain --.

Signed and Sealed this

Twentieth Day of February, 2007

JON W. DUDAS
*Director of the United States Patent and Trademark Office*